US007160552B2

(12) United States Patent
Miller et al.

(10) Patent No.: US 7,160,552 B2
(45) Date of Patent: Jan. 9, 2007

(54) METHOD OF FEEDING A RUMINANT

(75) Inventors: Bill L. Miller, Fort Dodge, IA (US); H. Bruce Perry, Webster City, IA (US); Thomas Edward Johnson, Thor, IA (US)

(73) Assignee: Land O'Lakes Purina Feed LLC, Shoreview, MN (US)

( * ) Notice: Subject to any disclaimer, the term of this patent is extended or adjusted under 35 U.S.C. 154(b) by 607 days.

(21) Appl. No.: 10/094,228

(22) Filed: Mar. 8, 2002

(65) Prior Publication Data

US 2003/0068390 A1 Apr. 10, 2003

Related U.S. Application Data

(60) Provisional application No. 60/274,847, filed on Mar. 9, 2001.

(51) Int. Cl.
A23K 1/18 (2006.01)
(52) U.S. Cl. ............... 424/438; 424/738; 426/2; 426/35; 514/23; 514/25; 514/57
(58) Field of Classification Search ............... 426/26, 426/35; 424/438, 738; 514/23, 25, 53, 54, 514/57
See application file for complete search history.

(56) References Cited

U.S. PATENT DOCUMENTS

| | | | | |
|---|---|---|---|---|
| 4,600,585 A | * | 7/1986 | Vitcenda et al. | 426/2 |
| RE32,811 E | | 12/1988 | Rudin | 424/195.1 |
| 4,800,088 A | | 1/1989 | Sawhill | 426/69 |
| 4,820,527 A | | 4/1989 | Christensen et al. | 426/2 |
| 5,047,332 A | | 9/1991 | Chahal | 435/42 |
| 5,126,150 A | | 6/1992 | Piatt et al. | 426/94 |
| 5,234,687 A | | 8/1993 | Barbera et al. | 424/195.1 |
| 5,571,542 A | | 11/1996 | Miller et al. | 426/2 |
| 5,614,501 A | | 3/1997 | Richards | 514/22 |
| 5,662,901 A | | 9/1997 | Tobey, Jr. et al. | 424/94.2 |
| 5,720,971 A | | 2/1998 | Beauchemin et al. | 424/438 |
| 5,789,001 A | | 8/1998 | Klopfenstein et al. | 426/2 |
| 5,807,594 A | * | 9/1998 | King et al. | 426/2 |
| 5,851,573 A | | 12/1998 | Lepine et al. | 426/2 |
| 5,958,898 A | | 9/1999 | Hayek et al. | 514/54 |
| 6,066,341 A | | 5/2000 | Wilson | 424/680 |
| 6,087,092 A | | 7/2000 | Richards | 435/4 |
| 6,093,425 A | | 7/2000 | Kamarei | 426/72 |
| 6,114,609 A | | 9/2000 | Beck et al. | 800/320.1 |
| 6,162,473 A | | 12/2000 | Fodge et al. | 426/53 |
| 6,180,131 B1 | | 1/2001 | Sunvold et al. | 424/442 |
| 6,194,009 B1 | | 2/2001 | Kamarel | 426/72 |
| 6,238,708 B1 | | 5/2001 | Hayek et al. | 426/2 |
| 6,245,326 B1 | | 6/2001 | Topping et al. | 424/78.01 |

FOREIGN PATENT DOCUMENTS

| | | | |
|---|---|---|---|
| WO | 82/02650 | * | 8/1982 |
| WO | WO 82/02650 | | 8/1982 |
| WO | WO 00/53030 | | 9/2000 |

OTHER PUBLICATIONS

W. J. Miller. The University of Georgia College of Agriculture. Athems. GA. *Dairy Cattle Feeding and Nutrition*. Academic Press. New York. 3 pages (1979).
Macdonald Campus of McGill University. Section entitled *Calf Feeding & Management* from *Dairy Cattle Production* chapter. 24 pages ("Winter. 1990" according to Chhaya Sayala in the International Search Report of counterpart international application No. PCT/US02/07268: date offered subject to confirmation and or clarification by Applicant.).
B. J. Impex And Marketing Flyer entitled: *Psyllium Husks Powder High Fiber For A Good Diet*, obtained from Internet on Oct. 31, 2000 At http://www.bjimpex.com/psyllium. (1 Page).
Article entitled: *Psyllium*, obtained from Internet on Oct. 31, 2000 at http://psyllium.bestnutrition.com, (5 pages).
Article entitled: *Plantas Medicinales*, (Spanish) obtained from Internet on Mar. 2, 2001 at http:/www.cof.es/pam229/plantas-medicinales.htm. (9 pages). English language translation attached to Spanish language version (8 pages).
*Upbeat on Fiber: This Oldie-But-Goodie is Back on the Dietary Hit Parade, Food Insight* (4 pages) Aug. 1998.
Doyle, Peter, *Selection of Supplementary Feeds, Agriculture Western Australia-Farmnote*, vol. 65, pages 1 of 6 thru 5 of 6 (1991).
Racz, Vernon, J., *Canadian Field Peas, Nutrient Composition of Canadian Field Peas, Feed Resource Centre, Department of Animal and Poultry Science, University of Saskatchewan*, 6 pages (1995).
Professor Folke Tjerneld, *Hemicellulose and Hemicellulases*, Department Of Biochemistry, Chemical Center, Land University (4 pages); Aug. 27, 1998.
Article entitled: *Understanding Rumen Function*, obtained from Internet on Mar. 2, 2001 at http:/animsci.agrenv.mcgill.ca/courses/450/extra/feed_to_milk/carbo2.html, (4 pages).
*New Processes for Generating Valuable Co-Products from Corn Fiber*, obtained from Internet on Mar. 2, 2001 at http:/www.nal.usda.gov/ttic/biofuels/hicks.htm, pp. 1-3; Progress reports listed for Jan. 1996-Sep. 1996, Jan. 1995-Dec. 1995 and Jan. 1994-May 1994.
Final Rule in 21 C.F.R. Part 101 published in Federal Register at 63 FR 8103 on Feb. 19, 1998, Psyllium Health Claim, (36 pages).
Linn, J.G.,, et al., *Feeding the Dairy Herd*, Feeding and Nutrition, 1988, 69 pages (as obtained from the Internet).
Minutes of Eastern Expert Committee on Cereals and Oilseeds, Annual Meeting, Feb. 6-8, 2000, 49 pages (as obtained from the Internet).
The Merck Index, An Encyclopedia of Chemicals, Drugs, and Biologicals, Eleventh Edition, 1989, p. 733.
Coughlon, Michael P. and Hazlewood, Geoffrey P.; *Hemicellulose and Hemicellulases*, pp. 1-143. (Portland Press, London and Chapel Hill), 1993.

* cited by examiner

*Primary Examiner*—Neil S. Levy
(74) *Attorney, Agent, or Firm*—Philip F. Fox

(57) ABSTRACT

A method of feeding ruminants, the method including feeding a ruminant a fluid animal feed during a feeding period, the fluid animal feed including an animal feed component and the ruminant consuming greater than about 1.25 pounds of the animal feed component per day, based on the dry weight of the animal feed component, during the feeding period; and the method further including feeding the ruminant a psyllium composition during the feeding period.

69 Claims, No Drawings

METHOD OF FEEDING A RUMINANT

CROSS-REFERENCE TO RELATED APPLICATION(S)

This application claims priority from U.S. Provisional Patent Application Ser. No. 60/274,847 that was filed on Mar. 9, 2001.

BACKGROUND OF THE INVENTION

The present invention generally relates to a method of feeding ruminants. More particularly, the present invention relates to a method of feeding ruminants, especially prior to weaning, an animal feed that contains a component, such as a psyllium composition, with a substantial hemicellulose content.

Ruminants, such as cattle, have a four compartment stomach, as opposed to the single stomach that human beings have. Two of these stomach compartments are the abomasum and the rumen. In a mature ruminant, fermentation of feed in the rumen provides the majority of energy and protein to the ruminant. On the other hand, in a newborn ruminant, the rumen is substantially undeveloped and the abomasum is the primary stomach compartment for digestion and nutrient assimilation. Consequently, young ruminants are typically fed a liquid diet containing readily digestible nutrients, since the abomasum is incapable of digesting sufficient amounts of more complex nutrients that typically form the majority of the nutrition found in solid feeds.

While being fed the liquid diet that is digestible in the abomasum, young ruminants are gradually introduced to a solid feed that contains readily digestible carbohydrates to support development of the rumen. Volatile fatty acids produced during fermentation of readily digestible carbohydrates support rumen tissue development and therefore control the rate of rumen development. Also, volatile fatty acids that are produced in the rumen help support development of microorganisms that break down the solid feed and transform components of the solid feed into microbial protein and volatile fatty acids. After the rumen has developed sufficiently to support the nutritional requirements of the young ruminant, the liquid diet is typically withdrawn and the nutritional requirements of the young ruminant are thereafter generally supplied by solid feed.

Weaning occurs when the liquid feed is withdrawn from the diet of the young ruminant. Thus, as used herein, "pre-weaning period" refers to the period when nutrients are predominantly or entirely supplied in liquid form to the ruminant, such as the calf, as part of a liquid feed, and "post-weaning period" refers to the period when nutrients are no longer predominantly or entirely provided to the ruminant, such as the calf, in the form of liquid feed. The post-weaning period is sometimes also referred to as the "ruminant period."

The pre-weaning period may also be broken down into a pre-ruminant period and a transition period. The "pre-ruminant period" is the time period when only nutrients in liquid form (as the liquid feed) are provided to the young ruminant. The "transition period" is the time period when the young ruminant is continuing to receive liquid nutrients while also receiving gradually increasing amounts of solid feed, such as dry calf starter, to support development of the rumen in anticipation of weaning. The transition period (and thus also the pre-weaning period) ends, and the post-weaning period (also referred to as the ruminant period) begins when the liquid feed that supplies liquid nutrients is predominantly or entirely withdrawn from the young ruminant's diet and the young ruminant is predominantly or entirely fed only solid feed, such as dry calf starter.

Typical liquid feeds for young ruminants include fluid milk or fluid milk replacers. Fluid milk replacers are frequently substituted in place of fluid milk because fluid milk that is produced by mature, lactating ruminants is generally more valuable when sold to consumers or when used to manufacture food products that are sold to consumers. Thus, fluid milk replacers that are produced to simulate fluid milk are generally substituted in place of fluid milk for feeding young ruminants. Fluid milk replacers may be based upon dairy components and non-dairy components that are combined to provide nutrient and palatability characteristics approximating the nutrient and palatability characteristics of fluid milk. Milk replacers are typically marketed in powdered form to avoid the higher transportation and storage costs of distributing fluid milk replacer. Powdered milk replacers are mixed with water prior to use to form fluid milk replacers that are provided to the young ruminants. The formulation and feeding of fluid milk replacers is well-known in the art.

Ruminants, such as cattle, are commonly bred and raised to produce food products, such as milk and beef, for human consumption. Maturation of cattle, as evidenced by weight gain, is an important factor that helps determine when a cow is ready to produce milk or is ready for market. Dairy farmers and cattle ranchers are greatly interested in techniques for economically achieving enhanced rates of ruminant weight gain, since such techniques beneficially reduce milk and beef production costs.

Also, dairy farmers and cattle ranchers recognize that the care and feeding of cattle both prior to weaning and after weaning play an important role in determining the amount and quality of products produced by the cattle. As an example, the age of dairy cows at freshening and the onset of lactation may be reduced by modifying the nutrient mix and nutrient composition in feed the dairy cows consume and by inducing the cows to gain weight more quickly during the pre-weaning and post-weaning periods prior to freshening. Also, in cattle ranching operations, increasing the rate of weight gain by young cattle beneficially reduces the time required for producing cattle with a size that is suitable for market.

Furthermore, in both dairy operations and ranching operations, it is generally desirable to increase the feed efficiency of young ruminants. As used herein, the term "feed efficiency" refers to the ratio, over a select time period for one or more particular ruminants, of (1) the weight gained by the ruminant(s), versus (2) the weight of feed consumed by the ruminant(s). As the ruminants more efficiently transform ingested feed into weight gain, the feed efficiency ratio, and consequently the feed efficiency, of the ruminant(s) increases, since less feed by the ruminant(s) is required to attain a unit amount of weight gain.

A major overall desire of dairy farmers and ranchers alike is to reduce the overall cost to produce a product, such as milk or beef, with an acceptable level of quality. Depending upon numerous cost variables, such as the cost of feed, labor costs on the farm or ranch, and equipment and building costs on the farm or ranch, this desired cost reduction may be achieved by increasing the rate of weight gain by young ruminants and/or increasing the feed efficiency of young ruminants. Thus, dairy farmers and ranchers, depending upon their particular cost variables, may employ either enhanced rates of weight gain or increased feed efficiency or a combination of enhanced rates of weight gain and increased feed efficiency to reduce the cost of bringing milk and beef to the consumer market.

To complement liquid feeds that are fed to ruminants, such as cattle, prior to weaning, a number of additives and supplements have been developed for feeding calves along with the liquid feed during the pre-weaning period. These additives and supplements have been developed for a number of different purposes. For example, some additives and supplements have been developed to generally enhance the health of the young calves or help prevent or control development of specific conditions or ailments, such as scours. Additionally, some additives or supplements have been developed in an attempt to enhance appetite, enhance maturation rate, and/or enhance weight gain.

In this regard, various veterinary pharmaceutical compositions have been developed to help prevent or inhibit development of certain ailments in ruminants. Also, numerous vitamin compositions have been developed to help enhance the general health of ruminants and/or to help prevent or inhibit development of ailments or conditions in ruminants. Finally, the use of psyllium has been prescribed for reducing scours in calves, and a *Plantago* seed supplement has been described to help reduce animal stress conditions, prevent or treat scours, and promote growth of ruminants. Also, psyllium incorporation in the diet of ruminants has been described for increasing the rate of weight gain per unit weight of protein that is consumed by ruminants.

Though the various ruminant feed supplements and additives that have been proposed and/or practiced over the years have enhanced the overall knowledge base with respect to ruminant feeding, these feed supplements and additives, as well as feeding techniques that employ these feed supplements and additives, have not yet fully identified, addressed, or optimized options for increasing the rate of weight gain exhibited by ruminants or for increasing the feed efficiency of ruminants. Thus, dairy farmers and ranchers alike are still in need of a new approach to feeding ruminants that enhances weight gain rates in ruminants and/or increases the feed efficiency of ruminants. The method of the present invention achieves enhanced ruminant weight gain rates and achieves increased ruminant feed efficiencies and thereby satisfies this need of dairy farmers and ranchers.

BRIEF SUMMARY OF THE INVENTION

The present invention includes a method of feeding a ruminant. The method entails feeding the ruminant a fluid animal feed during a feeding period where the fluid animal feed includes an animal feed component and the ruminant consumes the animal feed component at greater than about 1.25 pounds of the animal feed component per day, based on the dry weight of the animal feed component, during the feeding period. The method further entails feeding the ruminant a psyllium composition during the feeding period. The present invention further includes a ruminant ration and a daily ruminant ration.

DETAILED DESCRIPTION

The present invention generally relates to a method of feeding ruminants. More particularly, the present invention relates to a method of feeding ruminants, especially prior to weaning, an animal feed that contains a component, such as a psyllium composition, with a substantial hemicellulose content.

The method of the present invention includes (1) feeding young ruminants according to a first feeding regimen prior to weaning during a pre-weaning period and (2) feeding young ruminants according to a second feeding regimen after weaning during a post-weaning period. During the pre-weaning period, the ruminants are fed a fluid animal feed and a dry animal feed, along with a supplemental feed material. The supplemental feed material may be supplied separately from the fluid animal feed, but is preferably supplied to the ruminants as part of the fluid animal feed. On the other hand, during the post-weaning period, the ruminants are fed the dry animal feed, and optionally may be fed some plant-based haylage and/or silage, such as grass hay. In addition, during both the pre-weaning period and the post-weaning period, the ruminants have free access to water ad libitum.

Weaning occurs when the liquid feed is withdrawn from the diet of the young ruminants. Thus, as used herein, the term "pre-weaning period" refers to the period when nutrients are predominantly or entirely supplied to the ruminant, such as the calf, in liquid form, as part of a liquid feed, and the term "post-weaning period" refers to the period when nutrients are no longer predominantly or entirely provided to the ruminant, such as the calf, in the form of liquid feed. The post-weaning period is sometimes also referred to as the "ruminant period."

During the post-weaning period, the ruminants are preferably not fed any of the fluid animal feed and the ruminants are preferably not fed any of the supplemental feed material. If the ruminants are nonetheless fed some of the fluid animal feed and/or some of the supplemental feed material during the post-weaning period, the ruminants are fed only an insignificant or de minimis amount of the fluid animal feed and/or less than an effective amount of the supplemental feed material. The term "effective amount of the supplemental feed material" is subsequently defined herein.

Preferably, during the post-weaning period, the ruminants are not fed any of the fluid animal feed since such feeding of fluid animal feed during the post-weaning period is not presently believed necessary to achieve the benefits of the present invention and therefore would unnecessarily increase the cost and complexity of feeding the ruminants. Also, the ruminants are preferably not fed any of the fluid animal feed during the post-weaning period since such feeding of fluid animal feed during the post-weaning period may cause the ruminants to ingest less feed that is destined for digestion in the rumen. Likewise, the supplemental feed material is preferably excluded from the second feeding regimen of the ruminants during the post-weaning period, since incorporation of the supplemental feed material is not believed necessary for achieving the benefits of the present invention and therefore would unnecessarily increase the cost of feeding the ruminants.

The fluid animal feed that is provided during the pre-weaning period may generally include any fluid milk replacer that provides a level of nutrition to ruminants that is sufficient to support the nutritional requirements of the ruminants during the pre-weaning period. The fluid milk replacer may be liquid milk replacer, rehydrated milk replacer that is formed by rehydrating dry or powdered milk replacer, or a combination of liquid milk replacer and rehydrated milk replacer. As used herein, the term "liquid milk replacer" refers to milk replacer that is in liquid form when purchased. Often, if not predominantly, liquid milk replacer is based upon dry or powdered milk replacer that has been rehydrated. As used herein, the term "rehydrated milk replacer" refers to milk replacer that is prepared as a liquid, after purchase or preparation of the dry or powdered milk replacer, by rehydrating the dry or powdered milk replacer.

The supplemental feed material is preferably provided to the ruminants as part of the fluid animal feed, though the supplemental feed material may optionally be provided separately from the fluid animal feed. The fluid animal feed may, and preferably does, include antibiotics to help control scours and enhance the respiratory health of the ruminants. Some non-exhaustive examples of desirable antibiotics include Neomycin and Oxytetracycline, which are preferably provided in the fluid animal feed in combination with each other.

The fluid animal feed may optionally also include any other nutritional component that is capable of remaining dissolved or in suspension in the fluid animal feed. Some non-exhaustive examples of other nutritional components that are typically capable of remaining dissolved or in suspension in the fluid animal feed and that may therefore typically be incorporated as part of the fluid animal feed include sugar(s); sugar solution(s); sugar alcohol(s); protein material(s), such as vegetable protein material(s), animal protein material(s), and marine protein material(s); bean-based or grain-based oil(s); bean-based or grain-based meal (s); bean-based or grain-based syrup(s); fatty acid(s); and any of these in any combination. Preferably, however, the fluid animal feed primarily consists of, and more preferably consists essentially of, the fluid milk replacer, any optionally added antibiotics, and the supplemental feed material.

The fluid milk replacer, when purchased as liquid milk replacer, may generally be any commercially available liquid milk replacer. The fluid milk replacer, when prepared from powdered or dry milk replacer, may be formulated and prepared as the rehydrated milk replacer by those responsible for feeding the ruminants. Some examples of suitable powdered milk replacers for forming the rehydrated milk replacer include AMPLIFIER® MAX NT powdered milk replacer, AMPLIFIER® Select NT powdered milk replacer, MAXI CARE® NT powdered milk replacer, and Nursing Formula™ NT powdered milk replacer that are each available from Land O'Lakes, Inc. of Arden Hills, Minn.

The fluid milk replacer may generally include any concentration of crude protein. However, the fluid milk replacer preferably contains about 16 to about 35 weight percent crude protein, based upon the total dry weight of the fluid milk replacer, to help optimize weight gain in the ruminants. Likewise, the fluid milk replacer may contain any concentration of fat, but preferably contains about to about 20 weight percent fat, based upon the total dry weight of the fluid milk replacer, to increase the energy content of the fluid milk replacer, help reduce the incidence of scours in the ruminants, and inhibit deleterious effects of any stress the ruminants experience.

Some examples of preferred fat sources for the fluid milk replacer are edible lard and high quality vegetable fats that may be used individually or in any combination. The fat in the fluid milk replacer is preferably homogenized to reduce the particle size of the fat and enhance the digestibility of the fat. One preferred form of the fluid milk replacer includes about 28 weight percent crude protein and about 20 weight percent fat, based upon the total dry weight of the fluid milk replacer.

If dry or powdered milk replacer is used, the dry or powdered milk replacer may be rehydrated with water or any edible aqueous fluid, such as fluid milk, to form the fluid milk replacer. The concentration of the dry or powdered milk replacer in the water or aqueous fluid may be varied in any ratio, depending upon the desired concentration of nutrients in the fluid milk replacer and the desired consistency of the fluid milk replacer. Preferably, however, the powdered or dry milk replacer is rehydrated in water to form fluid milk replacer having a total solids concentration ranging from about 10 weight percent to about 20 weight percent, based upon the total weight of the fluid milk replacer. Of course, rehydrated milk replacer may also be combined with liquid milk replacer to form the fluid milk replacer. Likewise, dry or powdered milk replacer maybe rehydrated by combining dry or powdered milk replacer with liquid milk replacer and, optionally, additional water and/or additional aqueous fluid.

The supplemental feed material that is fed to the ruminants during the pre-weaning period may generally be any material that includes a substantial amount of hemicellulose, though the supplemental feed material preferably contains at least about 50 weight percent hemicellulose and more preferably contains at least about 60 weight percent hemicellulose, based upon the dry weight of the supplemental feed material. Still more preferably, the supplemental feed material predominantly comprises hemicellulose. Hemicellulose is actually a family of branched, low molecular weight polysaccharides that are associated with cellulose and lignin in plant cell walls. Hemicellulose molecules are, as compared to cellulose molecules, highly complex molecules and are built up from several different monosaccharides, such as xylose, mannose, galactose, glucose, arabinose, and methylglucoronic acid.

One example of the supplemental feed material that comprises a suitable amount of hemicellulose is a psyllium composition that contains psyllium. Psyllium is a non-digestible, water-soluble fiber. Psyllium is sometimes employed in human and veterinary medicine due to the laxative properties of psyllium. Psyllium is derived from the seed coat or husk of psyllium seed. Psyllium seed is produced by plants of the *Plantago genus*. Various species of the *Plantago genus* are known, such as *Plantago lanceolate, Plantago rugelii,* and *Plantago major*. Some exemplary species of the *Plantago genus* that are sources of commercially available psyllium include *Plantago indica, Plantago psyllium,* and *Plantago ovatao*. One preferred source of psyllium are seeds from the *Plantago ovata* species, which is sometimes referred to as indian or blonde psyllium, Forskal psyllium, or Ispaghaula. Forskal psyllium has one of the highest contents of hemicellulose of the known types of psyllium. One exemplary source of the psyllium composition is PS Fiber, Inc. of Muncie, Ind.

The psyllium composition should generally have a purity of at least about 80 weight percent, based upon the total dry weight of the psyllium composition. As used herein, the term "purity," when used in regard to the psyllium composition, refers to the concentration of psyllium in the psyllium composition. Preferably, the psyllium composition has a purity of at least about 90 weight percent, and more preferably at least about 95 weight percent, based upon the total dry weight of the psyllium composition. In addition to psyllium, the psyllium composition preferably contains less than about 15 weight percent light extraneous matter and less than about one percent heavy extraneous matter, based upon the total dry weight of the psyllium composition. More preferably, the light extraneous matter and the heavy extraneous matter collectively make up less than about 10 weight percent of the psyllium composition, and still more preferably collectively make up less than about 5 weight percent of the psyllium composition, based upon the total dry weight of the psyllium composition. Light extraneous matter comprises fibrous material associated with the seed husk of the psyllium seed, and heavy extraneous matter comprises seed fragments and soil.

The psyllium composition should be in the form of a powder with a fine particle size to help maintain the particles of psyllium in solution when combined with water and help enhance the rate of water absorption, and the amount of water absorbed, by the psyllium. The psyllium composition is preferably ground to allow at least about 90 weight percent of the psyllium composition to pass through a Bureau of Standards Sieve Number 100 mesh screen from the U.S. Standard Sieve Series. More preferably, the psyllium composition is milled to allow at least about 99 weight percent, and still more preferably, 100 weight percent, of the psyllium composition to pass through the Bureau of Standards Sieve Number 100 mesh screen from the U.S. Standard Sieve Series. Additionally, the psyllium composition preferably has a swell volume that ranges from about 49 to about 104 milliliters of water per gram of the psyllium composition, and an average swell volume ranging from about 57 to about 86 milliliters of water per gram of the psyllium composition.

Thus, psyllium is a hemicellulose source (or more properly the sole hemicellulose source) of the psyllium composition. When psyllium is the only hemicellulose source present in the psyllium composition, the psyllium composition is consequently the supplemental feed material. When the supplemental feed material that includes the substantial amount of hemicellulose includes a hemicellulose source or sources other than, or in addition to, the psyllium composition, the supplemental feed material should generally have a purity of at least about 80 weight percent, based upon the total dry weight of the supplemental feed material. The term "purity," when used in relation to the supplemental feed material that includes one or more hemicellulose sources in addition to or other than psyllium, refers to the total concentration of all hemicellulose sources, collectively, in the supplemental feed material. Preferably, when the supplemental feed material includes a hemicellulose source or sources other than or in addition to psyllium, the supplemental feed material has a purity of at least about 90 weight percent, and more preferably at least about 95 weight percent, based upon the total dry weight of the supplemental feed material.

The supplemental feed material that includes a hemicellulose source or sources other than or in addition to psyllium should be in the form of a powder with a fine particle size to help maintain the particles of the hemicellulose source(s) in solution when combined with water and help enhance the rate of water absorption, and the amount of water absorbed, by the hemicellulose source(s). The supplemental feed material that includes a hemicellulose source or sources other than or in addition to psyllium is preferably ground to allow at least about 90 weight percent of the supplemental feed material to pass through a Bureau of Standards Sieve Number 100 mesh screen from the U.S. Standard Sieve Series. More preferably, the supplemental feed material that includes a hemicellulose source or sources other than or in addition to psyllium is milled to allow at least about 99 weight percent, and still more preferably, 100 weight percent, of the supplemental feed material to pass through the Bureau of Standards Sieve Number 100 mesh screen from the U.S. Standard Sieve Series. Additionally, the supplemental feed material that includes a hemicellulose source or sources other than or in addition to psyllium preferably has a swell volume that ranges from about 49 to about 104 milliliters of water per gram of the supplemental feed material, and an average swell volume ranging from about 57 to about 86 milliliters of water per gram of the supplemental feed material.

Generally, any dry animal feed that is effective, when consumed, to supply the nutritional requirements of growing ruminants may be fed to the ruminants during the pre-weaning period and during the post-weaning period. The dry animal feed should be palatable to the ruminants so that the ruminants readily ingest the dry animal feed. Also, the dry animal feed should provide an adequate amount of energy to the ruminants in the form of readily fermentable carbohydrates that support rapid rumen development.

Typically, suitable dry animal feed, such as calf starter for calves, contains anywhere from about 16 weight percent crude protein to about 28 weight percent crude protein, based upon the total dry weight of the dry animal feed. Preferably, the dry animal feed contains at least about 26 weight percent crude protein and more preferably about 26 weight percent to about 28 weight percent crude protein, based upon the total dry weight of the dry animal feed.

Some non-exhaustive examples of suitable dry animal feeds for calves destined for dairy production include FUTURE COW® STARTER™ calf starter, SWEET START SUPREME™ calf starter, 16% Calf Starter/Grower starter feed, CALF PRIMER™ TCR I calf starter, CALF PRIMER™ TCR II calf starter, and Future Cow Mixer calf starter, each of which are available from Land O'Lakes, Inc. of Arden Hills, Minn. Also, some non-exhaustive examples of suitable dry animal feeds for calves destined for beef production include STEAKMAKER START'EM calf starter, STEAKMAKER 2× START'EM calf starter, HEAD START calf starter, HEAD START LFW WCS calf starter, HEAD START LF calf starter, and HEAD START WCS calf starter that are each available from Land O'Lakes, Inc. of Arden Hills, Minn.

In addition to the dry animal feed, the second feeding regimen may also incorporate some plant-based haylage and/or silage, such as grass hay, to address any digestion issues, such as the potential for bloating, that may arise during the post-weaning period. One typical cause of bloating in ruminants is rapid intake of immature, highly nutritious green legumes (alfalfa or clovers) by the ruminants. These plants, when in a vegetative state, contribute high levels of ruminally degradable protein and high levels of carbohydrates and are digested quite rapidly in the rumen. This rapid digestion may cause bloat by dropping the pH of fluid in the rumen, increasing gas production in the rumen, and binding protein molecules into a surface film over the ruminal contents that eventually traps gas in the rumen. Grasses, such as that in the form of grass hay, have lower protein content than legumes and may therefore be used to help satisfy ruminant desires for eating plants while minimizing the potential for bloating to occur.

The fluid animal feed may be prepared by combining the animal feed component, such as powdered or dry milk replacer, and, optionally any other nutritional component(s). Preferably, the supplemental feed material, such as the psyllium composition, is also incorporated in the fluid animal feed. As used herein, the term "animal feed component" generally refers, collectively, to any and all milk replacer(s), such as dry or powdered milk replacer(s), fluid milk replacer(s), liquid milk replacer(s), and/or rehydrated milk replacer(s) incorporated in the fluid animal feed. The fluid animal feed should include an effective amount of the animal feed component. The term "effective amount of the animal feed component" is defined subsequently herein.

The supplemental feed material, such as the psyllium composition, that is employed in the present invention provides optimum results when mixed with a dry form of the animal feed component, such as powdered or dry milk replacer. Thus, the supplemental feed material is preferably incorporated in the fluid animal feed. Mixing the supplemental feed material with a dry form of the animal feed component prior to addition of water simplifies the distribution and use of the fluid animal feed. In particular, the mixture of the supplemental feed material and the dry form of the animal feed component, may be transported as a pre-mixed composition that is later combined with water (or an aqueous fluid) so that the person supplying the fluid animal feed to the ruminants does not have to accurately mix the animal feed component and the supplemental feed material prior to feeding the fluid animal feed to the ruminants.

Shortly, before feeding the ruminants the fluid animal feed, the mixture of the supplemental feed material and the dry form of the animal feed component may be mixed with an effective amount of water to form the fluid animal feed. As used herein, the term "effective amount of water" means an amount of water that is sufficient to provide the fluid animal feed with a texture and consistency that is similar to the texture and consistency of fluid milk. Of course, besides water, the "effective amount of water" takes into account the water content of any aqueous fluid other than, or in addition to, water that is combined with the dry form of the animal feed component.

As used herein, the term "ruminant" means an even-toed, hoofed animal that has a complex 3- or 4-chamber stomach and that typically re-chews what the ruminant has previously swallowed. Some non-exhaustive examples of ruminants include cattle, sheep, goats, oxen, musk, ox, llamas, alpacas, guanicos, deer, bison, antelopes, camels, and giraffes. The digestive tract of a cow, one example of the ruminant that may be fed in accordance with the present invention, includes a stomach that has four different components: a rumen, a reticulum, an omasum, and an abomasum. The four sections of the stomach may affect digestion of a component passing through the stomach because each section of the stomach serves a different function in the digestive process.

In the rumen, food is mixed with the saliva and then churned in a coordinated motion. The food mixture undergoes some fermentation and bacterial digestion in the rumen. Also, portions of the food mixture that enter the rumen with an excessively large particle size are formed into a cud that the ruminant regurgitates and rechews to reduce the particle size. Properly sized food that leaves the rumen passes from the rumen through the reticulum and into the omasum. While in the omasum, the food mixture is mixed to maintain the food mixture in a homogenous state and to remove excess fluid. Then, the homogenous mixture is passed from the omasum to the abomasum where gastric digestion occurs.

During the pre-weaning period, under feeding regimens currently employed in the dairy industry, ruminants are typically fed the animal feed component, such as the fluid milk replacer, at rates that extend up to about 1.25 pounds of the animal feed component, per day, based upon the dry weight of the animal feed component. Consequently, any feeding rate during the pre-weaning period ranging up to about 1.25 pounds of the animal feed component, such as the milk replacer, per day, based upon the dry weight of the animal feed component, falls within the meaning of the term "conventional feeding rate," as defined herein, for the animal feed component, such as the milk replacer, and any feeding rate during the pre-weaning period above about 1.25 pounds of the animal feed component, such as the milk replacer, per day, based upon the dry weight of the animal feed component, falls within the meaning of the term "enhanced feeding rate," as defined herein, for the animal feed component, such as the milk replacer, unless otherwise specified.

Preferably, the enhanced feeding rate for the animal feed component is at least about 1.5 pounds of the animal feed component, such as the milk replacer, per day, based on the dry weight of the animal feed component, during the pre-weaning period. More preferably, the enhanced feeding rate for the animal feed component is at least about 2.5 pounds of the animal feed component, such as the milk replacer, per day, based on the dry weight of the animal feed component, during the pre-weaning period. Still more preferably, the enhanced feeding rate for the animal feed component is at least about 2.9 pounds of the animal feed component, such as the milk replacer, per day, based on the dry weight of the animal feed component, during the pre-weaning period.

When provided along with the animal feed component that is fed at the enhanced feeding rate, the effective amount of the supplemental feed material generally need not exceed about 30 grams of the supplemental feed material, such as the psyllium composition, per calf per day, during the pre-weaning period, and may be as low as about 1 (or even less than 1) gram of the supplemental feed material, such as the psyllium composition, per calf per day, during the pre-weaning period, so long as some amount of the supplemental feed material, such as the psyllium composition, is provided to the calf during the pre-weaning period, preferably on daily basis. As one non-exhaustive exemplary range, when provided along with the animal feed component that is fed at the enhanced feeding rate, the effective amount of the supplemental feed material may range from about 5 grams to about 15 grams of the supplemental feed material, such as the psyllium composition, per calf per day, during the pre-weaning period.

As another non-exhaustive exemplary range, when provided along with the animal feed component that is fed at the enhanced feeding rate, the effective amount of the supplemental feed material preferably ranges from about 10 grams to about 15 grams of the supplemental feed material, such as the psyllium composition, per calf per day, during the pre-weaning period. As a non-exhaustive example from this preferred, non-exhaustive exemplary range, when provided along with the animal feed component that is fed at the enhanced feeding rate, the effective amount of the supplemental feed material is more preferably about 12.5 grams of the supplemental feed material, such as the psyllium composition, per calf per day, during the pre-weaning period.

For purposes of considering comparisons between ruminants that are fed in different ways, the "effective amount of the supplemental feed material" may be characterized as a "first effective amount of the supplemental feed material" or as a "second effective amount of the supplemental feed material," depending upon the particular comparison under consideration. Both the "first effective amount of the supplemental feed material" and the "second effective amount of the supplemental feed material" fall within the scope of the "effective amount of the supplemental feed material."

The first effective amount of the supplemental feed material maybe considered in a comparison of a first ruminant with a second ruminant, where the first ruminant is fed the first effective amount of the supplemental feed material in combination with the "effective amount of the animal feed component." When used in combination with the first effective amount of the supplemental feed material, the "effective amount of the animal feed component" is the amount of the animal feed component that is fed to the first ruminant during the time period when the supplemental feed material is fed to the first ruminant. When the effective amount of the animal feed component is used in combination with the first effective amount of the supplemental feed material, the animal feed component and the supplemental feed material are preferably fed to the first ruminant together as part of the fluid animal feed.

When used in combination with the first effective amount of the supplemental feed material, the animal feed component is preferably fed to the first ruminant at the enhanced feeding rate (above about 1.25 pounds of the animal feed component per day, based upon the dry weight of the animal feed component) for the animal feed component. More preferably, in combination with the first effective amount of the supplemental feed material, the enhanced feeding rate for the animal feed component is at least about 1.5 pounds of the animal feed component per day, still more preferably at least about 2.5 pounds of the animal feed component per day, and even more preferably at least about 2.9 pounds of the animal feed component per day, based upon the dry weight of the animal feed component.

Thus, when provided along with the first effective amount of the supplemental feed material, the effective amount of the animal feed component will preferably be above about 1.25 pounds of the animal feed component per calf per day, more preferably at least about 1.5 pounds of the animal feed component per calf day, still more preferably at least about 2.5 pounds of the animal feed component per calf per day, and even more preferably at least about 2.9 pounds of the animal feed component per calf per day, based upon the dry weight of the animal feed component. Nevertheless, when provided along with the first effective amount of the supplemental feed material, it is believed the effective amount of the animal feed component may sometimes permissibly be about 1.25 pounds, or less, of the animal feed component per calf per day.

Taking these considerations into account, the "first effective amount of the supplemental feed material," as used herein, means an amount of the supplemental feed material that, when fed during the pre-weaning period along with the effective amount of the animal feed component to the first ruminant:

(1) that is fed an equal amount of the same, or substantially the same, animal feed component as the second ruminant, where the animal feed component is also fed at an equal rate to both the first ruminant and the second ruminant, (2) while the first ruminant and the second ruminant have equal access to the same, or substantially the same, dry animal feed, such as the same, or substantially the same, calf starter, and (3) while the first ruminant and the second ruminant also have equal access to water ad libitum, is effective to cause at least one, preferably at least two, more preferably at least three, still more preferably at least four, and most preferably all five of the following improvements that are listed in (a), (b), (c), (d), and (e) below:

(a) an increased total dry animal feed intake (weight basis) by the first ruminant, versus the total dry animal feed intake (weight basis) by the second ruminant, as measured over a segment of the pre-weaning period, preferably over a seven week segment of the pre-weaning period, and more preferably over the entire pre-weaning period, (b) an increased total dry animal feed intake (weight basis) by the first ruminant, versus the total dry animal feed intake (weight basis) by the second ruminant, as measured over a segment of the post-weaning period, preferably over a 16 week segment of the post-weaning period, and more preferably over the first 16 weeks of the post-weaning period, (c) a larger amount of weight gain by the first ruminant versus the amount of weight gain by the second ruminant as measured over a segment of the post-weaning period, preferably over a 16 week segment of the post-weaning period, and more preferably over the first 16 weeks of the post-weaning period, (d) a larger amount of weight gain by the first ruminant versus the amount of weight gain by the second ruminant as measured over a time period that extends from the pre-weaning period and into the post-weaning period, preferably over a 23 week time period that extends from the pre-weaning period and into the post-weaning period, more preferably over the entire pre-weaning period and at least part of the post-weaning period, and still more preferably over the entire pre-weaning period and the first 16 weeks of the post-weaning period, and/or (e) a feed efficiency during a segment of the post-weaning period that is greater for the first ruminant versus the feed efficiency exhibited by the second ruminant during this segment of the post-weaning period, where the segment is preferably a 16 week segment of the post-weaning period and is more preferably the first 16 weeks of the post-weaning period.

The first effective amount of the supplemental feed material, in combination with the "effective amount of the animal feed component," is preferably sufficient to cause the dry animal feed intake (weight basis) by the first ruminant to increase by at least about 5 percent, more preferably by at least about 10 percent, and still more preferably by at least about 22 percent, as compared to the dry animal feed intake (weight basis) of the second ruminant, over a segment of the pre-weaning period, preferably over a seven week segment of the pre-weaning period, and more preferably over the entire pre-weaning period.

Also, the first effective amount of the supplemental feed material, in combination with the "effective amount of the animal feed component," is preferably sufficient to cause the dry animal feed intake (weight basis) of the first ruminant to increase by at least about 5 percent over the dry animal feed intake (weight basis) of the second ruminant as measured over a segment of the post-weaning period, preferably over a 16 week segment of the post-weaning period, and more preferably over the first 16 weeks of the post-weaning period. Next, the first effective amount of the supplemental feed material, in combination with the "effective amount of the animal feed component," is preferably sufficient to cause the first ruminant to gain about 5 percent more weight, and more preferably more than about 8 percent more weight, than the second ruminant as measured over a segment of the post-weaning period, preferably over a 16 week segment of the post-weaning period, and more preferably over the first 16 weeks of the post-weaning period.

Additionally, the first effective amount of the supplemental feed material, in combination with the "effective amount of the animal feed component," is preferably sufficient to cause the first ruminant to gain at least about 5 percent more weight, and more preferably at least about 7 percent more weight, than the second ruminant, as measured over a period that extends from the pre-weaning period and into the post-weaning period, preferably over a 23 week period that extends from the pre-weaning period and into the post-weaning period, more preferably over the entire pre-weaning period and at least part of the post-weaning period, and still more preferably over the entire pre-weaning period and the first 16 weeks of the post-weaning period. Finally, the first effective amount of the supplemental feed material, in combination with the "effective amount of the animal feed component," is preferably sufficient to cause the feed efficiency of the first ruminant to increase by at least about 3 percent, as compared to the feed efficiency of the second ruminant, as measured over a segment of the post-weaning period, preferably over a 16 week segment of the post-weaning period, and more preferably over the first 16 weeks of the post-weaning period.

For these comparisons of the first ruminant and the second ruminant that are provided above in regard to the first effective amount of the supplemental feed material and the effective amount of the animal feed component, the first ruminant and the second ruminant may be provided substantially the same animal feed component and substantially the same dry animal feed, but preferably are provided the same animal feed component and the same dry animal feed. Furthermore, in these comparisons of the first ruminant and the second ruminant that are provided above in regard to the first effective amount of the supplemental feed material and the effective amount of the animal feed component, the first ruminant and the second ruminant are preferably fed the same amount of the animal feed component, based upon the dry weight of the animal feed component, while the first ruminant and the second ruminant are given equal access to the dry animal feed and equal access to water ad libitum.

Furthermore, in these comparisons of the first ruminant and the second ruminant that are provided above in regard to the first effective amount of the supplemental feed material and the effective amount of the animal feed component, the first ruminant preferably, during the pre-weaning period, receives the fluid animal feed as a combination of the animal feed component and the supplemental feed material while also having continuing access to the dry animal feed. Also in these comparisons of the first ruminant and the second ruminant that are provided above in regard to the first effective amount of the supplemental feed material and the effective amount of the animal feed component, the second ruminant preferably, during the pre-weaning period, receives the animal feed component as the fluid animal feed while also having continuing access to the dry animal feed, but does not receive any of the supplemental feed material. On the other hand, in these comparisons of the first ruminant and the second ruminant that are provided above in regard to the first effective amount of the supplemental feed material and the effective amount of the animal feed component, the first ruminant and the second ruminant, during the post-weaning period, preferably have equal and continuous access to the dry animal feed and do not receive any of the animal feed component or any of the supplemental feed material.

Though these comparisons that are provided above in regard to the first effective amount of the supplemental feed material and the effective amount of the animal feed component are provided in terms of a first ruminant and a second ruminant, these comparisons are equally applicable to a first group of ruminants versus a second group of ruminants, respectively. In this comparison of groups of ruminants, the first group of ruminants and the second group of ruminants preferably include about the same number of ruminants, preferably include the same or similar species (or the same or about the same weighting of different species), and preferably each include ruminants with the same, or about the same, median age.

As another approach, the second effective amount of the supplemental feed material maybe considered in a comparison of the first ruminant with a third ruminant, where the first ruminant is fed the second effective amount of the supplemental feed material in combination with the "effective amount of the animal feed component." When used in combination with the second effective amount of the supplemental feed material, the "effective amount of the animal feed component" is the amount of the animal feed component that is fed to the first ruminant during the period when the supplemental feed material is fed to the first ruminant.

When the effective amount of the animal feed component is used in combination with the second effective amount of the supplemental feed material, the animal feed component and the supplemental feed material are preferably fed to the first ruminant together as part of the fluid animal feed. On the other hand, in comparisons of the first ruminant to the third ruminant, the third ruminant is fed the animal feed component at the conventional feeding rate (up to about 1.25 pounds of the animal feed component per day, based upon the dry weight of the animal feed component) for the animal feed component during the period when the supplemental feed material is fed to the first ruminant, and the third ruminant is not fed any of the supplemental feed material.

When used in combination with the second effective amount of the supplemental feed material, the animal feed component is fed to the first ruminant at the enhanced feeding rate (above about 1.25 pounds of the animal feed component per day, based upon the dry weight of the animal feed component) for the animal feed component. More preferably, in combination with the second effective amount of the supplemental feed material, the enhanced feeding rate for the animal feed component is at least about 1.5 pounds of the animal feed component per day, still more preferably at least about 2.5 pounds of the animal feed component per day, and even more preferably at least about 2.9 pounds of the animal feed component per day, based upon the dry weight of the animal feed component.

Thus, when provided along with the second effective amount of the supplemental feed material, the effective amount of the animal feed component will be above about 1.25 pounds of the animal feed component per calf per day. More preferably, when provided along with the second effective amount of the supplemental feed material, the effective amount of the animal feed component is at least about 1.5 pounds of the animal feed component per calf day, still more preferably at least about 2.5 pounds of the animal feed component per calf per day, and even more preferably at least about 2.9 pounds of the animal feed component per calf per day, based upon the dry weight of the animal feed component.

Taking these considerations into account, the "second effective amount of the supplemental feed material," as used herein, means an amount of the supplemental feed material that, when fed during the pre-weaning period along with the effective amount of the animal feed component to the first ruminant (1) that is fed the same, or substantially the same, animal feed component as the third ruminant, with the permissible exception of protein concentration, with the third ruminant being fed the animal feed component at the conventional feeding rate for the animal feed component, and with the first ruminant preferably being fed the animal feed component on at least the same number of days as the animal feed component is fed to the third ruminant, (2) while the first ruminant and the third ruminant have equal access to the same, or substantially the same, dry animal feed, such as the same, or substantially the same, calf starter, with the permissible exception of protein concentration, and (3) while the first ruminant and the third ruminant also have equal access to water ad libitum, is effective to cause at least one, preferably at least two, more preferably at least three, still more preferably at least four, and most preferably all five of the following improvements that are listed in (a), (b), (c), (d), and (e) below:

(a) an increased total dry animal feed intake (weight basis) by the first ruminant, versus the total dry animal feed intake (weight basis) by the third ruminant, as measured over a segment of the post-weaning period, preferably over a 16 week segment of the post-weaning period, and more preferably over the first 16 weeks of the post-weaning period, (b) a larger amount of weight gain by the first ruminant versus the amount of weight gain by the third ruminant as measured over a segment of the pre-weaning period, preferably over a 7 week segment of the pre-weaning period, and more preferably over the entire pre-weaning period, (c) a larger amount of weight gain by the first ruminant versus the amount of weight gain by the third ruminant as measured over a segment of the post-weaning period, preferably over a 16 week segment of the post-weaning period, and more preferably over the first 16 weeks of the post-weaning period, (d) a larger amount of weight gain by the first ruminant versus the amount of weight gain by the third ruminant as measured over a period that extends from the pre-weaning period and into the post-weaning period, preferably over a 23 week period that extends from the pre-weaning period and into the post-weaning period, more preferably over the entire pre-weaning period and at least part of the post-weaning period, and still more preferably over the entire pre-weaning period and the first 16 weeks of the post-weaning period, and/or (e) a feed efficiency during a segment of the pre-weaning period that is greater for the first ruminant versus the feed efficiency exhibited by the third ruminant during this segment of the pre-weaning period, where the segment is preferably a 7 week segment of the pre-weaning period and is more preferably the entire pre-weaning period.

The second effective amount of the supplemental feed material, in combination with the effective amount of the animal feed component, is preferably sufficient to cause the dry animal feed intake (weight basis) by the first ruminant to increase by at least about 9 percent, and more preferably by at least about 15 percent, as compared to the dry animal feed intake (weight basis) of the third ruminant over a segment of the post-weaning period, preferably over a 16 week segment of the post-weaning period, and more preferably over the first 16 weeks of the post-weaning period. Next, the second effective amount of the supplemental feed material, in combination with the effective amount of the animal feed component, is preferably sufficient to cause the first ruminant to experience at least about 64 percent more weight gain, and preferably at least about 96 percent more weight gain, than the weight gain experienced by the third ruminant, as measured over a segment of the pre-weaning period, preferably over a 7 week segment of the pre-weaning period, and more preferably over the entire pre-weaning period.

Additionally, the second effective amount of the supplemental feed material, in combination with the "effective amount of the animal feed component," is preferably sufficient to cause the first ruminant to gain at least about 5 percent more weight, and more preferably at least about 6 percent more weight, than the third ruminant, as measured over a segment of the post-weaning period, preferably over a 16 week segment of the post-weaning period, and more preferably over the first 16 weeks of the post-weaning period. Also, the second effective amount of the supplemental feed material, in combination with the "effective amount of the animal feed component," is preferably sufficient to cause the first ruminant to gain at least about 8 percent more weight, more preferably at least about 12 percent more weight, and still more preferably at least about 15 percent more weight than the third ruminant, as measured over a period that extends from the pre-weaning period and into the post-weaning period, preferably over a 23 week period that extends from the pre-weaning period and into the post-weaning period, more preferably over the entire pre-weaning period and at least part of the post-weaning period, and still more preferably over the entire pre-weaning period and the first 16 weeks of the post-weaning period.

Finally, the second effective amount of the supplemental feed material, in combination with the "effective amount of the animal feed component," is preferably sufficient to cause the feed efficiency of the first ruminant to increase by at least about 30 percent, preferably by at least about 38 percent, and more preferably by at least about 45 percent, as compared to the feed efficiency of the third ruminant, as measured over a segment of the pre-weaning period, preferably over a 7 week segment of the pre-weaning period, and more preferably over the entire pre-weaning period.

For these comparisons of the first ruminant and the third ruminant that are provided above in regard to the second effective amount of the supplemental feed material, the first ruminant and the third ruminant may be provided substantially the same animal feed component and substantially the same dry animal feed, but preferably are provided the same animal feed component and the same dry animal feed, with a couple of exceptions. First, the animal feed component that is fed to the first ruminant may have about 30 percent more protein content, on a weight basis, than the animal feed component that is fed to the third ruminant. Second, the dry animal feed that is fed to the first ruminant may have up to about 55 percent more protein content, on a weight basis, than the dry animal feed that is fed to the third ruminant.

Furthermore, in these comparisons of the first ruminant and the third ruminant that are provided above in regard to the second effective amount of the supplemental feed material, the third ruminant is fed the animal feed component at the conventional feeding rate (up to about 1.25 pounds of the animal feed component per day, based upon the dry weight of the animal feed component) for the animal feed component, and the animal feed component is preferably fed to the first ruminant for at least the same number of days that the animal feed component is fed to the third ruminant. On the other hand, in these comparisons of the first ruminant and the third ruminant that are provided above in regard to the second effective amount of the supplemental feed material, the first ruminant is fed the animal feed component at the enhanced feeding rate (more than about 1.25 pounds of the animal feed component per day, based upon the dry weight of the animal feed component) for the animal feed component, preferably during at least the period when the third ruminant is fed the animal feed component. In these comparisons of the first ruminant and the third ruminant that are provided above in regard to the second effective amount of the supplemental feed material, the first ruminant and the third ruminant, at all times, are given equal access to the dry animal feed and equal access to water ad libitum.

Furthermore, in these comparisons of the first ruminant and the third ruminant that are provided above in regard to the second effective amount of the supplemental feed material, the first ruminant preferably, during the pre-weaning period, receives the fluid animal feed as a combination of the animal feed component and the supplemental feed material while also having continuing access to the dry animal feed. Also in these comparisons of the first ruminant and the third ruminant that are provided above in regard to the second effective amount of the supplemental feed material, the third ruminant preferably, during the pre-weaning period, receives the animal feed component as the fluid animal feed while also having continuing access to the dry animal feed, but does not receive any of the supplemental feed material. On the other hand, in these comparisons of the first ruminant and the third ruminant that are provided above in regard to the second effective amount of the supplemental feed material, the first ruminant and the third ruminant, during the post-weaning period, preferably have equal and continuous access to the dry animal feed and do not receive any of the animal feed component and do not receive any of the supplemental feed material.

Though these comparisons that are provided above in regard to the second effective amount of the supplemental feed material are provided in terms of a first ruminant and a third ruminant, these comparisons are equally applicable to a first group of ruminants versus a third group of ruminants, respectively. In this comparison of groups of ruminants, the first group of ruminants and the third group of ruminants preferably include about the same number of ruminants, preferably include the same or similar species (or the same or about the same weighting of different species), and preferably each include ruminants with the same, or about the same, median age.

One product of the present invention may be characterized as a ruminant ration. The ruminant ration includes at least the animal feed component and the supplemental feed material, where the supplemental feed material and the animal feed component are preferably combined with each other, as previously discussed. Consistent with the discussions above, the concentration of the supplemental feed material may range up to about 5 weight percent (or even more) on a dry weight basis, based upon the dry weight of the animal feed component and the supplemental feed material collectively being 100 weight percent. Preferably, the concentration of the supplemental feed material ranges from about 0.4 weight percent to about 2.6 weight percent on a dry weight basis, based upon the dry weight of the animal feed component and the supplemental feed material collectively being 100 weight percent. Another product of the present invention may be characterized as a daily ration that may be fed to ruminants during the pre-weaning period. The daily ration includes at least the animal feed component and the supplemental feed material, where the supplemental feed material and the animal feed component are preferably combined with each other, as previously discussed. The amount of the animal feed component present in the daily ration is preferably greater than about 1.25 pounds, on a dry matter basis, during the pre-weaning period.

Various analytical techniques are employed herein. An explanation of these techniques follows. All values presented in this document for a particular parameter, such as weight percent total protein, weight percent fat, and weight percent total solids, are based on the "as is" sample and are therefore on a "wet basis", unless otherwise specified herein.

Property Determination & Characterization Techniques

To determine the dry weight of a particular sample, the sample is first weighed. The weighed sample is then dried in an oven at a temperature that is adequate to drive moisture from the sample without degrading the sample components, such as at a temperature ranging from about 100° C. to about 110° C. The oven drying is continued until the weight of the dried sample remains constant, despite additional oven drying.

To determine the weight percent total solids, wet basis, in a sample, the actual weight of total solids is determined by analyzing the sample in accordance with Method #925.23 (33.2.09) of *Official Methods of Analysis*, Association of Official Analytical Chemists (AOAC) (168 Ed., 1995). The weight percent total solids, wet basis, is then calculated by dividing the actual weight of total solids by the actual weight of the sample.

To determine the percent of total protein, wet basis, in a sample, the actual weight of total protein is determined in accordance with Method #991.20 (33.2.11) of *Official Methods of Analysis*, Association of Official Analytical Chemists (AOAC) ($16^{th}$ Ed., 1995). The value determined by the above method yields "total Kjeldahl nitrogen", which is ordinarily equivalent to "total protein" since the above method incorporates a factor that accounts for the average amount of nitrogen in protein. Since any and all total Kjeldahl Nitrogen determinations presented herein are based on the above method, and since the term "total protein" is sometimes also referred to as "crude protein", the terms "total Kjeldahl Nitrogen," "total protein," and "crude protein" are used interchangeably herein. The weight percent total protein, wet basis, is calculated by dividing the actual weight of total protein that is determined in accordance with this method by the total weight of the sample.

To determine the weight percent hemicellulose on a dry basis in a particular sample, one may first determine the weight percent Acid Detergent Fiber {% ADF (DM basis)}, on a dry matter basis, in the sample and the weight percent Neutral Detergent Fiber {% N.F. (DM basis)}, on a dry matter basis, in the sample. Then, the % ADF (DM basis) is subtracted from the % N.F. (DM basis) to calculate the weight percent hemicellulose, on a dry basis, in the sample. The % ADF (DM basis) and the % N.F. (DM basis) may be determined in accordance with published Forage Analysis Procedures (July, 1993) of the National Forage Testing Association.

The Forage Analysis Procedures (July, 1993) of the National Forage Testing Association are available on the Internet at the following web address:

http://www.foragetestinf.org./fap/index.html. The % ADF (DM basis) of a particular sample may be determined in accordance with the procedure set forth in §B(4. 1) of the Forage Analysis Procedures (July, 1993) that is entitled *Determination of Acid Detergent Fiber By Refluxing*. The % N.F. (DM basis) of a particular sample may be determined in accordance with the procedure set forth in §B(5.1) of the Forage Analysis Procedures (July, 1993) that is entitled *Determination of Amylase Neutral Detergent Fiber By Refluxing*. Appropriate sample preparation, quality assurance, and quality control procedures are also set forth in the Forage Analysis Procedures (July, 1993) of the National Forage Testing Association.

The present invention is more particularly described in the following Kay examples that are intended as illustrations only since numerous modifications and variations within the scope of the present invention will be apparent to those skilled in the art.

EXAMPLES

The examples provided below demonstrate the effect of feeding young calves, during the pre-weaning period, the supplemental feed material, such as the psyllium composition, along with calf milk replacer at an enhanced feeding rate of the calf milk replacer, as compared to the effect of feeding young calves, during the pre-weaning period, either (1) calf milk replacer at an enhanced feeding rate of the calf milk replacer, but without the psyllium composition (supplemental feed material), or (2) calf milk replacer at a conventional feeding rate of the calf milk replacer and without the psyllium composition (supplemental feed material).

In each of the Examples provided below, test cattle were first weighed upon arrival at the test facility and were also weighed at the beginning of the first week of the pre-weaning period and at the end of each week throughout the pre-weaning period and the post-weaning period. At the beginning of the eighth week of testing, all of the calves had been fully weaned and began the 16-week post-weaning period. Besides weight, other performance parameters were determined on a daily basis and memorialized at the end of each week during the pre-weaning period and at the end of each week during the post-weaning period.

All data that is provided in Tables 1–20 below is based upon individual data for each calf, then-present, as least square means of the particular data over all calves present in the test at the time the particular data was recorded. Data for parameters presented in Tables 1–20 was analyzed using the general linear model (GLM) statistical procedure of SAS™ statistical analysis software for a randomized complete block design that included both the particular feed regimen and the week of the test period in the model statement. The SAS™ statistical analysis software is available from SAS Institute, Inc. of Cary, N.C. Additionally, all data was analyzed to determine the mean of the data for each variable under consideration during the collection period for the particular data.

Additionally, the PDiff function of the GLM statistical procedure was used to characterize the mean Values of the data by providing for comparisons between mean data values for the calves of different treatments for particular test parameters or variables. The probability value P is a measure of the statistical probability that the differing parameter values between (1) the animals fed the psyllium composition and fed calf milk replacer at the enhanced feeding rate of the calf milk replacer, (2) the control animals not fed the psyllium composition, but fed calf milk replacer at the enhanced feeding rate of the calf milk replacer, and (3) the control animals not fed the psyllium composition, and fed calf milk replacer at the conventional feeding rate of the calf milk replacer may be explained by the difference between receiving the psyllium composition and not receiving the psyllium composition and the differences in calf milk replacer feeding rates.

A P value of 0.05 means that five times out of 100 the results can be explained by factors other than differences between the different treatments. Likewise, a P value of 0.77 means that 77 times out of 100, the difference in value between the control group and the group fed the psyllium composition may be explained by factors other than the differing feeding regimens. For purposes of comparing data in this document, P values of 0.10, or lower, are considered to be statistically significant. Thus, where a P value of 0.10 or less is returned for a particular variable, it is assumed that the differing results are fully explained by the test regimen, i.e.: the presence or lack of the psyllium composition along with any differences in the calf milk replacer feeding rate.

Also, many of Tables 1–20 include a coefficient of variation for data in a particular row. A coefficient of variation is simply the standard deviation of a particular variable that is divided by the mean of the variable and then multiplied by 100. Because variances and standard deviations are used to measure error, and because these values for variances and standard deviations are sensitive to the absolute scale of the variable, coefficients of variations are provided, since coefficients of variation remove the influence of the overall magnitude of the data.

Example 1

This example demonstrates the effect of feeding young, calves, during the pre-weaning period, calf milk replacer at an enhanced rate of about 2.90 pounds of calf milk replacer per day, on a dry weight basis, along with a psyllium composition. In this example, sixty (60) Holstein bull calves from California ranging in age from 3 days old to 110 days old and averaging about 100 pounds each, with a range of about 95 pounds to about 105 pounds each, were assigned to one of three different treatments. A first treatment is referred to herein as "Control #1A", a second treatment is referred to herein as "Control #1B", and a third treatment is referred to herein as "Psyllium Test #1".

Gamma globulin, as measured by the Zinc Sulfate Turbidity test and expressed in weight percent gamma globulin, was initially determined for each calf. Thereafter, each calf was assigned, in terms of the gamma globulin concentration for the calf, to either level (1), level (2), level (3), level (4), or level (5), where level (1) included gamma globulin concentrations ranging from 0.00 to 0.49 weight percent; level (2) included gamma globulin concentrations ranging from 0.50 to 0.99 weight percent; level (3) included gamma globulin concentrations ranging from 1.00 to 1.49 weight percent; level (4) included gamma globulin concentrations ranging from 1.50 to 2.49 weight percent; and level (5) included gamma globulin concentrations of 2.5 weight percent or higher. Equal numbers of calves from the level (1) gamma globulin concentration range were placed in the three different treatments (Control #1A, Control #1B and Psyllium Test #1); equal numbers of calves from the level (2) gamma globulin concentration range were placed in the three different treatments; equal numbers of calves from the level (3) gamma globulin concentration range were placed in the three different treatments; equal numbers of calves from the level (4) gamma globulin concentration range were placed in the three different treatments; and equal numbers of calves from the level (5) gamma globulin concentration range were placed in the three different treatments.

The calves from the three different treatments were each fed and monitored during both the pre-weaning period and the post-weaning period. Details about the handling and feed consumption for the calves of these three different treatments during the pre-weaning period are provided in Tables 1–7 below, while details about the handling and feed consumption of the calves during the post-weaning period are provided in Tables 7–10 below. The pre-weaning period and the post-weaning period for the handling and feed consumption details of Example 1 spanned a total of 23 weeks for the calves of Control #1A, Control #1B and Psyllium Test #1. The pre-weaning period lasted seven weeks, and the post-weaning period lasted sixteen weeks, though the calves of Control #1A were generally only fed the fluid animal feed through the sixth week of the pre-weaning period.

During the pre-weaning period, each of the calves of the three different treatments had continuing and equal access to a calf starter that is referred to in Table 1 below as "total calf ration." Also, during the pre-weaning period, each calf of each treatment had continuing and equal access to fresh water, ad libitum. The total calf ration fed to the calves of Control #1A during the pre-weaning period was pelleted; contained about 18 weight percent crude protein, based upon the total dry weight of the total calf ration; and also included about 90 grams of lasalocid per ton of total calf ration, based upon the as-fed weight of the total calf ration. Lasalocid is an additive that aids in prevention of coccidiosis and also helps improve feed efficiency in cattle. The total calf ration that was fed to the calves of Control #1 B and Psyllium Test #1 during the pre-weaning period was also pelleted; contained about 28 weight percent crude protein, based upon the weight of the total calf ration; and contained about 90 grams of lasalocid per ton of the total calf ration, based upon the as-fed weight of the total calf ration.

The calves of the three different treatments each received calf milk replacer during the pre-weaning period. The calf milk replacer that was provided to the calves of Control #1A had a crude protein concentration of about 22 weight percent, based upon the dry weight of the calf milk replacer, and a fat concentration of about 20 weight percent, based upon the dry weight of the calf milk replacer. The calf milk replacer that was fed to the calves of Control #1B and Psyllium Test #1 had a crude protein concentration of about 28 weight percent, based upon the dry weight of the calf milk replacer, and a fat concentration of about 20 weight percent, based upon the dry weight of the calf milk replacer.

The calf milk replacer was fed to the calves of Control #1A in two equal feedings at an overall rate of about 1.25 pounds of calf milk replacer per calf per day (about 0.625 pounds of calf milk replacer per calf per feeding of calf milk replacer), based upon the dry weight of the calf milk replacer. The calf milk replacer was fed to the calves of Control #1B and to the calves of Psyllium Test #1 in two equal feedings at an overall rate of about 2.90 pounds of calf milk replacer per calf per day (about 1.45 pounds of calf milk replacer per calf per feeding of calf milk replacer), based upon the dry weight of the calf milk replacer. Thus, the calf milk replacer was fed to the calves of Control #1B and the calves of Psyllium Test #1 at the "enhanced feeding rate" for the calf milk replacer, and the calf milk replacer was fed to the calves of Control #1A at the "conventional feeding rate" for the calf milk replacer.

In Example 1, the calves of Control #1 A and of Control #1B did not receive any of the psyllium composition during the pre-weaning period or, for that matter, during the post-weaning period. On the other hand, the calves of Psyllium Test #1 received about 6.24 grams of psyllium composition per calf per calf milk replacer feeding, or about 12.48 grams of psyllium composition per calf per day, during the pre-weaning period. The calf milk replacer originated as powdered milk replacer that was rehydrated prior to being fed to the calves. The calf milk replacer was rehydrated with water to form rehydrated milk replacer having a total solids concentration ranging from about 10 weight percent to about 20 weight percent, based upon the total weight of the rehydrated milk replacer. For the calves of Psyllium Test #1 that received the psyllium composition, the psyllium composition was added by hand to the powdered milk replacer before the powdered milk replacer was rehydrated.

The psyllium composition that was fed to the calves of Psyllium Test #1 had a purity of about 95 weight percent, based upon the total weight of the psyllium composition, which means that the psyllium composition contained about 95 weight percent psyllium and also included about 5 weight percent of light extraneous matter and/or heavy extraneous matter, based upon the total weight of the psyllium composition. The psyllium composition was milled to allow 100 percent of the psyllium composition to pass through a Bureau of Standards Sieve Number 100 mesh screen from the U.S. Standard Sieve Series. The swell volume of the psyllium composition ranged from about 49.1 milliliters of water per gram of the psyllium composition to about 62.9 milliliters of water per gram of the psyllium composition, with an average swell volume of about 57.4 milliliters of water per gram of the psyllium composition.

The fluid animal feed that was fed to the calves of Control #1A and Control #1B included the rehydrated milk replacer (also referred to herein as the fluid milk replacer), along with a small amount of antibiotics, and did not contain any of the psyllium composition. The fluid animal feed that was fed to the calves of Psyllium Test #1 included the rehydrated milk replacer, a small amount of the antibiotics, and the psyllium composition.

The antibiotics used for the calves of Control #1A, Control #1B, and Psyllium Test #1 consisted of a blend of Neomycin and Oxytetracycline. The antibiotic blend was added at a different concentration to the fluid animal feed that was fed to the calves of Control #1A versus the concentration of antibiotic added to the fluid animal feed that was fed to the calves of Control #1B and Psyllium Test #1 to cause each calf in each of the three different treatments to receive the same daily dosage of each of the antibiotics of the antibiotic blend.

For the calves of Control #1A, the Neomycin was included in the fluid animal feed at the rate of 400 grams of Neomycin per ton of powdered milk replacer, based upon the dry weight of the powdered milk replacer, and the Oxytetracycline was included in the fluid animal feed at the rate of 200 grams of Oxytetracycline per ton of powdered milk replacer, based upon the dry weight of the powdered milk replacer. On the other hand, for the calves of Control #1B and Psyllium Test #1, the Neomycin was included in the fluid animal feed at the rate of 172 grams of Neomycin per ton of powdered milk replacer, based upon the dry weight of the powdered milk replacer, and the Oxytetracycline was included in the fluid animal feed at the rate of 86 grams of Oxytetracycline per ton of the powdered milk replacer, based upon the dry weight of the powdered milk replacer.

The fluid animal feed was individually fed to each of the calves in each of the three different treatments twice per day at about 7:30 a.m. and again at about 4:00 p.m. Each of the calves of each of the treatments quickly consumed all of their particular allotment of the fluid animal feed within a few minutes of being provided with the fluid animal feed. Also, the calves of each of the three different treatments were, as previously indicated, given continuous and equal access to dry animal feed (the calf starter or total calf ration) and fresh water. Furthermore, each test calf in the three different treatments received veterinary care and management consistent with appropriate recommendations in the

*Guide for the Care and Use of Agricultural Animals in Agricultural Research and Teaching.* (1$^{st}$ Edition, March 1988).

All calves in the three different treatments were fully weaned from the fluid animal feed by the end of the seventh week of the pre-weaning period. The fluid animal feed was generally withdrawn from the calves of Control #1A at the end of the sixth week of the pre-weaning period, whereas the fluid animal feed was generally withdrawn from the calves of Control #1B and Psyllium Test #1 at the end of the seventh week of the pre-weaning period, though the calves of the Control #1B and Psyllium Test #1 only received one feeding of the fluid animal feed per day (about 1.45 pounds of calf milk replacer per calf per feeding of calf milk replacer, based upon the dry weight of the calf milk replacer) during the seventh week of the pre-weaning period.

Details about the diet of the calves during the pre-weaning period and details about the calf milk replacer component of the fluid animal feed for the three different treatments are provided in Tables 1 and 2 below.

TABLE 1

Diet During Pre-Weaning Period of Example 1

| Treatment Name | Milk Replacer (MR) Description | Total Calf Ration (TCR) | Number of Calves |
|---|---|---|---|
| Control #1A | 22:20 All Milk$^A$ 1.25#/calf/day$^B$ | Yes$^C$ | 20 |
| Control #1B | 28:20 All Milk$^D$ 2.90#/calf/day$^E$ | Yes$^F$ | 20 |
| Psyllium Test #1 | 28:20 All Milk$^D$ 2 90#/calf/day$^E$ w/Psyllium$^G$ | Yes$^F$ | 20 |

$^A$NT 400:200 (Neomycin/Oxytetracycline @ 400/200 grams/ton)
$^B$Calves were weaned at 6 weeks provided they were eating over 1.0 pound of Total Calf Ration per day. Starting at week 8, calves were moved to a nearby facility. The trial was terminated after 23 weeks on test
$^C$Total Calf Ration (pelleted), 18% crude protein, with 90 g/ton lasalocid
$^D$NT 172:86 (Neomycin/Oxytetracycline @ 172/86 grams/ton)
$^E$Calves were fed in the a.m. only (1.45#/calf/day) during week 7. Starting at week 8, calves weaned and moved to the nearby facility
$^F$Total Calf Ration (pelleted), 28% crude protein, with 90 g/ton lasalocid
$^G$Hand added at 6 24 g/calf/feeding. Psyllium had a purity of 95% and was milled so that 100% passed through a Bureau of Standards Sieve Number 100 mesh screen f/the U.S. Standard Sieve Series Swell volumes ranged from 49 1–62 9 ml per gram (x = 57 4 ml/gram)

TABLE 2

Milk Replacer Feeding Details During Pre-Weaning Period of Example 1

| Description | | Control #1A | Control #1B | Psyllium Test #1 |
|---|---|---|---|---|
| Weight Percent Milk Replacer Powder In Fluid Milk Replacer$^a$ | | 13 51 | 17 16 | 17 16 |
| Milk Replacer Fed Twice Daily (Period 1 Thru Period 6)$^C$ | Pounds of Milk Replacer Powder Per Milk Replacer Feeding$^A$ | 0 625 | 1 45 | 1 45 |
| | Pounds of Water Per Milk Replacer Feeding$^A$ | 4 00 | 7 00 | 7 00 |
| | Pounds of Fluid Milk Replacer Per Milk Replacer Feeding$^A$ | 4 625 | 8 45 | 8 45 |
| Total Pounds of Milk Replacer Powder Fed During Periods 1–6 (on a Dry Matter Basis) | | 52.5 | 121 8 | 121 8 |
| Milk Replacer | Pounds of Milk | 0 0 | 1 45 | 1 45 |

TABLE 2-continued

Milk Replacer Feeding Details During Pre-Weaning Period of Example 1

| Description | | Control #1A | Control #1B | Psyllium Test #1 |
|---|---|---|---|---|
| Fed Once Daily (Period 7)$^C$ | Replacer Powder Per Milk Replacer Feeding$^B$ | | | |
| | Pounds of Water Per Milk Replacer Feeding$^B$ | 0.0 | 7 00 | 7 00 |
| | Pounds of Fluid Milk Replacer Per Milk Replacer Feeding$^B$ | 0 0 | 8 45 | 8 45 |
| Total Pounds of Milk Replacer Powder Fed During Period 7 (on a Dry Matter Basis) | | 0 0 | 10 2 | 10 2 |
| Total Pounds of Milk Replacer Powder Fed During Periods 1–7 (on a Dry Matter Basis) | | 52 5 | 132 0 | 132 0 |

$^A$Two Feedings of Milk Replacer per day for Control #1A, Control #1B, and Psyllium Test #1 during Period 1 thru Period 6
$^B$One Feeding of Milk Replacer per day For Control #1B & Psyllium Test #1 during Period 7, No feedings of Milk Replacer For Control #1A during Period 7
$^C$Each period had a seven day duration
$^a$Based on the total weight of the Fluid Milk Replacer Next, details about the average weight gain per calf during the seven individual weeks of the pre-weaning period along with an average total weight gain per calf over the entire pre-weaning period are provided in Table 3 below:

TABLE 3

Weight Gain During Pre-Weaning Period of Example 1

| | Control #1A | Control #1B | Psyllium Test #1 | Coefficient of Variation (C.V.) |
|---|---|---|---|---|
| Average Gain Per Calf During Period 1$^A$ (lbs) | 0.32$^b$ | 7.86$^a$ | 6.14$^a$ | 103.58 |
| Average Gain Per Calf During Period 2$^A$ (lbs) | 1.05$^b$ | 9.87$^a$ | 8.93$^a$ | 77.09 |
| Average Gain Per Calf During Period 3$^A$ (lbs) | 6.54$^b$ | 11.32$^a$ | 12.96$^a$ | 57.55 |
| Average Gain Per Calf During Period 4$^A$ (lbs) | 7.54$^b$ | 14.58$^a$ | 12.65$^a$ | 39.91 |
| Average Gain Per Calf During Period 5$^A$ (lbs) | 7.93$^b$ | 12.74$^a$ | 12.52$^a$ | 29.24 |
| Average Gain Per Calf During Period 6$^A$ (lbs) | 11.08$^b$ | 8.76$^b$ | 13.86$^a$ | 32.86 |
| Average Gain Per Calf During Period 7$^A$ (lbs) | 4.00$^b$ | 9.42$^a$ | 8.32$^a$ | 89.02 |
| Average Total Gain Per Calf During Period 1 Through Period 7 (lbs) | 38.45$^b$ | 74.54$^a$ | 75.38$^a$ | 20.79 |

$^A$Each period had a seven day duration
$^{a,b}$Numbers within the same row with different single letter superscripts differ at a probability value of $P < 0.05$ The data presented in Table 3 shows that the differences in the feeding regimens between Psyllium Test #1 and Control #1B caused a slight increase in the average total weight gain per calf during the pre-weaning period for the calves of Psyllium Test #1, versus the calves of Control #1B. However, these results of Table 3 show a dramatic increase in average total weight gain per calf during the pre-weaning period for the calves of Psyllium Test #1 versus the calves of Control #1A of about 96 percent (75.38 pounds versus 38.45 pounds).

Next, details about the average milk replacer consumption per calf during the seven individual weeks of the pre-weaning period and over the entire pre-weaning period are provided in Table 4 below:

TABLE 4

Milk Replacer Consumption During Pre-Weaning Period of Example 1

|  | Control #1A | Control #1B | Psyllium Test #1 | Coefficient of Variation (C.V.) |
|---|---|---|---|---|
| Average Milk Replacer Consumption[A] Per Calf During Period 1[B] (lbs) | 8 10[b] | 13 84[a] | 14.73[a] | 16.48 |
| Average Milk Replacer Consumption[A] Per Calf During Period 2[B] (lbs) | 8 49[b] | 14.69[a] | 14 49[a] | 20.82 |
| Average Milk Replacer Consumption[A] Per Calf During Period 3[B] (lbs) | 8 56[b] | 18 79[a] | 18 20[a] | 12.08 |
| Average Milk Replacer Consumption[A] Per Calf During Period 4[B] (lbs) | 8 62[b] | 19 05[a] | 18.49[a] | 12.45 |
| Average Milk Replacer Consumption[A] Per Calf During Period 5[B] (lbs) | 8 67[b] | 19.49[a] | 19 09[a] | 9.15 |
| Average Milk Replacer Consumption[A] Per Calf During Period 6[B] (lbs) | 8 69[b] | 18.88[a] | 19 19[a] | 9.93 |
| Average Milk Replacer Consumption[A] Per Calf During Period 7[B] (lbs) | 0 24[b] | 10.11[a] | 10.11[a] | 4.61 |
| Average Total Milk Replacer Consumption[A] Per Calf During Period 1 Through Period 7 (lbs) | 51.36[b] | 114 85[a] | 114 29[a] | 8.95 |

[A]Milk Replacer Consumption Weight is provided on a dry matter (dm) basis
[B]Each period had a seven day duration.
[a,b]Numbers within the same row with different single letter superscripts differ at a probability value of P < 0.05

Next, details about the average amount of dry feed consumption during the seven individual weeks of the pre-weaning period and over the entire pre-weaning period are provided in Table 5 below:

TABLE 5

Dry Feed Consumption During Pre-Weaning Period of Example 1

|  | Control #1A | Control #1B | Psyllium Test #1 | Coefficient of Variation (C.V.) |
|---|---|---|---|---|
| Average Dry Feed[A] Consumption[B] Per Calf During Period 1[C] (lbs) | 0 26 | 0.28 | 0.32 | 122.01 |
| Average Dry Feed[A] Consumption[B] Per Calf During Period 2[C] (lbs) | 1.26 | 1.33 | 1.31 | 89.51 |

TABLE 5-continued

Dry Feed Consumption During Pre-Weaning Period of Example 1

|  | Control #1A | Control #1B | Psyllium Test #1 | Coefficient of Variation (C.V.) |
|---|---|---|---|---|
| Average Dry Feed[A] Consumption[B] Per Calf During Period 3[C] (lbs) | 3.62[a] | 1.88[b] | 2.67[ab] | 64.04 |
| Average Dry Feed[A] Consumption[B] Per Calf During Period 4[C] (lbs) | 6 27[a] | 2 62[b] | 3.69[b] | 59.26 |
| Average Dry Feed[A] Consumption[B] Per Calf During Period 5[C] (lbs) | 6 92[a] | 3 69[b] | 4.41[b] | 40.89 |
| Average Dry Feed[A] Consumption[B] Per Calf During Period 6[C] (lbs) | 9 40[a] | 4.85[b] | 6 08[b] | 52.09 |
| Average Dry Feed[A] Consumption[B] Per Calf During Period 7[C] (lbs) | 18.78[a] | 10.74[b] | 12.47[b] | 35.13 |
| Average Total Dry Feed[A] Consumption[B] Per Calf During Period 1 Through Period 7 (lbs) | 46 51[a] | 25.38[b] | 30.95[b] | 39.17 |

[A]Dry Feed for Control #1A was Total Calf Ration (pelleted), 18% crude protein. with 90 g/ton lasalocid, Dry Feed for Control #1B & Psyllium Test #1 was Total Calf Ration (pelleted), 28% crude protein, with 90 g/ton lasalocid
[B]Dry Feed Weight is provided on a dry matter (dm) basis
[C]Each period had a seven day duration
[a,b]Numbers within the same row with different single letter superscripts differ at a probability value of P < 0.05

The details presented in Table 5 above demonstrate that the feeding regimen of Psyllium Test #1 versus the feeding regimen of Control #1B contributed to an increase of about 22 percent in the average total dry feed consumption of the calves of Psyllium Test #1 versus the calves of Control #1B.

Next, weight, weight gain, and feed efficiency details during the pre-weaning period are provided in Table 6 below:

TABLE 6

Feed Efficiency During Pre-Weaning Period of Example 1

|  | Control #1A | Control #1B | Psyllium Test #1 | Coefficient of Variation (C.V.) |
|---|---|---|---|---|
| Average Intial Ig[A] For All Calves | 3.47 | 3.67 | 3 47 | 39 78 |
| Average[B] Initial Weight Per Calf, lbs. (at start of period 1) | 107 1 | 105.7 | 107 3 | 3.03 |
| Average[C] Ending Weight Per Calf, lbs. (at end of period 7) | 145.5[b] | 180.9[a] | 182 2[a] | 2 97 |
| Average[D] Total Gain Per Calf During Period 1 Through Period 7 (lbs) | 38 45[b] | 74 54[a] | 75 38[a] | 20 79 |

TABLE 6-continued

Feed Efficiency During Pre-Weaning Period of Example 1

|  | Control #1A | Control #1B | Psyllium Test #1 | Coefficient of Variation (C.V.) |
|---|---|---|---|---|
| Feed Efficiency Average[E] During Periods 1–7 | 0 366[a] | 0 526[b] | 0 505[b] | 20 08 |

[A]Expressed in weight percent, as measured by Zinc Sulfate Turbidity test, then assigned to level 1, level 2, level 3, level 4, or level 5 as follows (1) Ig = 0.00–0.49, (2) Ig = 0.50–0.99, (3) Ig = 1.00–1.49, (4) Ig = 1.50–2.49, (5) Ig = 2.5 and higher
[B]The inital weight(s) of calves that were present in period 1 but did not complete period 7 are not included in this average
[C]This average excludes calves that were present in period 1 but did not complete period 7
[D]This average will not necessarily equal the value obtained by subtracting the average initial weight per calf (at start of period 1) from the average ending weight per calf (at the end of period 7), since this average is the sum of the weekly average gains per calf for periods 1–7 which may include one or more calves that did not finish period 7
[E]The Feed Efficiency Average is a ratio of the weight gained versus the weight of feed consumed. The Feed Efficiency Average During Periods 1–7 is the mean of all Feed Efficiency Averages during each of the individual periods (1–7) for each individual calf
[a,b]Numbers within the same row with different single letter superscripts differ at a probability value of $P < 0.05$ These details of Table 6 demonstrate that the feed efficiency average for the calves of Psyllium Test #1 improved by about 38 percent, versus the feed efficiency average for the calves of Control #1A, over the entire pre-weaning period.

Next, details about average calf weights during the pre-weaning and post-weaning periods of Example 1 are provided in Table 7 below:

TABLE 7

Average Calf Weight During Pre-Weaning & Post Weaning Periods of Example 1

|  | Control #1A | Control #1B | Psyllium Test #1 | Coefficient of Variation (C.V.) |
|---|---|---|---|---|
| Average[A] Weight Per Calf at Start of Period 1 (pounds) | 107.1 | 105.7 | 107.3 | 3.03 |
| Average[A] Weight Per Calf at Start of Period 8 and End of Period 7 (pounds) | 145.5[b] | 180.9[a] | 182.2[d] | 2.97 |
| Average[B] Weight Per Calf at End of Period 23 (pounds) | 468.5[c] | 496 58[b] | 525.3[a] | 2.79 |

[A]This average excludes calves that were present in period 1 but did not complete period 7
[B]This average excludes calves that were present in period 1 but did not complete period 23
[a,b]Numbers within the same row with different single letter superscripts differ at a probability value of $P < 0 05$ As indicated by the superscript letters A and B, the average weights of calves are presented for different points in time during the test regimen and exclude any calf or calves not present at the end of a period over which a particular measurement was made or averaged, even though that calf was present or those calves were present at the start of the period over which the particular measurement was made or averaged. This phenomena, which also exists in some other tables of this and other examples herein, merely recognizes that there is virtually always some degree of mortality in young calves, whether those calves are involved in testing of different feeding regimens or are merely being fed outside of an experimental test regimen. Typically, in the experience of the inventors, mortality rates for calves generally range from about five percent up to about twenty percent, during mid-length testing programs, such as in the twenty-three week long testing of Example 1.

Tables 8 through 10 that are provided below present details about weight gain, feed consumption, and feed efficiency during the sixteen weeks of the post-weaning period and also present data on the weight gain and the feed efficiency over the entire twenty-three week composite of the pre-weaning period and the post-weaning period. During the post-weaning period, none of the calves of any of the three testing regimens received any of the fluid animal feed (and thus did not receive any of the calf milk replacer) or any of the psyllium composition.

Also, during the post-weaning period, the calves of each of the three testing regimens had equal access to the total calf ration that served as the dry animal feed. The total calf ration of the post-weaning period was the same as the total calf ration of the pre-weaning period for the calves of Control #1A, Control #1B, and Psyllium Test #1, with the exception that the total calf ration was texturized during the post-weaning period and, as previously explained, was pelleted during the pre-weaning period. Also, the calves of Control #1A, Control #1B, and Psyllium Test #1 had continuous and equal access to fresh water ad libitum during the post-weaning period. Finally, starting with week fifteen (week 8 of the post-weaning period), chopped grass hay was offered at a low rate to the calves of the three different treatments to address digestion issues, such as the potential for bloating.

Weight gain details for the sixteen different weeks of the post-weaning period, over the entire post-weaning period, and over the composite of the pre-weaning and post-weaning periods are provided in Table 8 below:

TABLE 8

Weight Gain During Post-Weaning Period of Example 1

| Period[A] |  | Control #1A[B] | Control #1B[C] | Psyllium Test #1[C] | Coefficient of Variation (C.V.) |
|---|---|---|---|---|---|
| 8[A] | Average Daily Gain Per Calf (lbs) | 2 64[a] | 0 75[b] | 1 75[a] | 30.94 |
|  | Average Total Gain Per Calf During Period (lbs) | 18 50[a] | 5 23[b] | 12 28[a] |  |

TABLE 8-continued

Weight Gain During Post-Weaning Period of Example 1

| Period[A] | | Control #1A[B] | Control #1B[C] | Psyllium Test #1[C] | Coefficient of Variation (C.V.) |
|---|---|---|---|---|---|
| 9[A] | Average Daily Gain Per Calf (lbs) | 2 42 | 3 43 | 2 80 | 26.60 |
| | Average Total Gain Per Calf During Period (lbs) | 16 93 | 24 03 | 19 60 | |
| 10[A] | Average Daily Gain Per Calf (lbs) | 2 80[b] | 3 04[ab] | 3 75[a] | 14.89 |
| | Average Total Gain Per Calf During Period (lbs) | 19 58[b] | 21 28[ab] | 26 25[a] | |
| 11[A] | Average Daily Gain Per Calf (lbs) | 2 26 | 2 51 | 2 69 | 15.66 |
| | Average Total Gain Per Calf During Period (lbs) | 15 85 | 17 58 | 18 85 | |
| 12[A] | Average Daily Gain Per Calf (lbs) | 3 01 | 2 86 | 3 35 | 19.79 |
| | Average Total Gain Per Calf During Period (lbs) | 21 05 | 20 00 | 23 43 | |
| 13[A] | Average Daily Gain Per Calf (lbs) | 2 08 | 2 41 | 2 77 | 23.76 |
| | Average Total Gain Per Calf During Period (lbs) | 14 58 | 16 85 | 19 40 | |
| 14[A] | Average Daily Gain Per Calf (lbs) | 2 01 | 2 16 | 2 12 | 17.74 |
| | Average Total Gain Per Calf During Period (lbs) | 14 05 | 15 15 | 14 83 | |
| 15[A] | Average Daily Gain Per Calf (lbs) | 3 00 | 3 07 | 3 35 | 15 97 |
| | Average Total Gain Per Calf During Period (lbs) | 21 03 | 21 50 | 23 45 | |
| 16[A] | Average Daily Gain Per Calf (lbs) | 3 05 | 2 12 | 2 69 | 35.74 |
| | Average Total Gain Per Calf During Period (lbs) | 21 33 | 14 85 | 18 85 | |
| 17[A] | Average Daily Gain Per Calf (lbs) | 3 11 | 3 34 | 3 29 | 14.66 |
| | Average Total Gain Per Calf During Period (lbs) | 21 80 | 23 40 | 23 05 | |
| 18[A] | Average Daily Gain Per Calf (lbs) | 3 12 | 2 98 | 3 55 | 22.81 |
| | Average Total Gain Per Calf During Period (lbs) | 21 86 | 20 88 | 24 87 | |
| 19[A] | Average Daily Gain Per Calf (lbs) | 3 85 | 4 47 | 4 68 | 27 03 |
| | Average Total Gain Per Calf During Period (lbs) | 26 95 | 31 28 | 32 75 | |
| 20[A] | Average Daily Gain Per Calf (lbs) | 2 82 | 2 56 | 2 48 | 30.51 |
| | Average Total Gain Per Calf During Period (lbs) | 19 73 | 17 93 | 17 33 | |
| 21[A] | Average Daily Gain Per Calf (lbs) | 3 83 | 3 47 | 3 63 | 21.39 |
| | Average Total Gain Per Calf During Period (lbs) | 26 83 | 24 28 | 25 43 | |
| 22[A] | Average Daily Gain Per Calf (lbs) | 3 04 | 3 30 | 3 36 | 20.73 |
| | Average Total Gain Per Calf During Period (lbs) | 21 28 | 23 08 | 23 53 | |
| 23[A] | Average Daily Gain Per Calf (lbs) | 3 10 | 2 64 | 2 76 | 28.40 |
| | Average Total Gain Per Calf During Period (lbs) | 21 70 | 18 48 | 19 30 | |
| 8–23[A] | Average[D] Daily Gain Per Calf During Period 8 thru Period 23 (lbs) | 2 88[b] | 2 82[b] | 3 06[a] | 3.11 |
| | Average[E] Total Gain Per Calf During Period 8 thru Period 23 (lbs) | 322 98[b] | 315 73[b] | 343 15[a] | |
| 1–23[A] | Average[F] Daily Gain Per Calf During Period 1 thru Period 23 (lbs) | 2 24[c] | 2 43[b] | 2 60[a] | 4 06 |
| | Average[G] Total Gain Per Calf During Period 1 thru Period 23 (lbs) | 361 40[c] | 390 88[b] | 418 05[a] | |

[A]Each period had a seven day duration.
[B]Dry Feed for Control #1A during Periods 8–23 was Total Calf Ration (texturized), 18% crude protein, with 90 g/ton lasalocid
[C]Dry Feed for Control #1B & Psyllium Test #1 during Periods 8-23 was Total Calf Ration (texturized), 28% crude protein, with 90 g/ton lasalocid
[D]This average was calculated by dividing the Average Total Gain Per Day During Period 8 thru Period 23 by 112 (7 × 16)
[E]This average will not necessarily equal the value obtained by subtracting the average initial weight per calf (at start of period 8) from the average ending weight per calf (at the end of period 23), since this average is the sum of the weekly average gains per calf for periods 8–23 which may include one or more calves that did not finish period 23
[F]This average was calculated by dividing the Average Total Gain Per Day During Period 1 thru Period 23 by 161 (7 × 23)
[G]This average will not necessarily equal the value obtained by subtracting the average initial weight per calf (at start of period 1) from the average ending weight per calf (at the end of period 23), since this average is the sum of the weekly average gains per calf for periods 1–23 which may include one or more calves that did not finish period 23
[a,b]Numbers within the same row with different single letter superscripts differ at a probability value of $P < 0.05$ The details of Table 8 demonstrate that the average total weight gain per calf during the post-weaning period increased by about 6.2 percent for the calves of Psyllium Test #1 versus the calves of the Control #1A and increased by about 8.7 percent for the calves of Psyllium Test #1 versus the calves of Control #1B. Also, these details of Table 8 demonstrate that the average total weight gain per calf over the pre-weaning period and the post-weaning period, collectively, increased by more than 15 percent for the calves of Psyllium Test #1 versus the calves of Control #1A and increased by nearly seven percent for the calves of Psyllium Test #1 versus the calves of Control #1B.

Next, details about the dry animal feed (total calf ration) consumption during the sixteen individual weeks of the post-weaning period and over the entire post-weaning period are provided in Table 9 below:

TABLE 9

Dry Feed Consumption During Post-Weaning Period of Example 1

| | Control #1A | Control #1B | Psyllium Test #1 | Coefficient of Variation (C.V.) |
|---|---|---|---|---|
| Average Daily Dry Feed[A] Consumption[B] Per Calf During Period 8[C] (lbs) | 4 15 | 3 52 | 4 06 | 14 49 |
| Average Daily Dry Feed[A] Consumption[B] Per Calf During Period 9[C] (lbs) | 4 79 | 5 08 | 5 36 | 21 07 |
| Average Daily Dry Feed[A] Consumption[B] Per Calf During Period 10[C] (lbs) | 6 38[b] | 7 46[ab] | 7 82[a] | 9 08 |
| Average Daily Dry Feed[A] | 7 03[b] | 8 44[a] | 8 75[a] | 8 34 |

TABLE 9-continued

Dry Feed Consumption During Post-Weaning Period of Example 1

| | Control #1A | Control #1B | Psyllium Test #1 | Coefficient of Variation (C.V.) |
|---|---|---|---|---|
| Consumption[B] Per Calf During Period 11[C] (lbs) | | | | |
| Average Daily Dry Feed[A] Consumption[B] Per Calf During Period 12[C] (lbs) | 8 28[b] | 8 70[b] | 10 23[a] | 8 07 |
| Average Daily Dry Feed[A] Consumption[B] Per Calf During Period 13[C] (lbs) | 7 99[b] | 9 27[ab] | 9 97[a] | 12 23 |
| Average Daily Dry Feed[A] Consumption[B] Per Calf During Period 14[C] (lbs) | 9 23 | 10 28 | 10 81 | 14 22 |
| Average Daily Dry Feed[A,D] Consumption[B] Per Calf During Period 15[C] (lbs) | 9 35 | 10 54 | 10 54 | 7 57 |
| Average Daily Dry Feed[A,D] Consumption[B] Per Calf During Period 16[C] (lbs) | 11 13[b] | 11 96[ab] | 12 92[a] | 7 59 |
| Average Daily Dry Feed[A,D] Consumption[B] Per Calf During Period 17[C] (lbs) | 11 83[b] | 13 08[ab] | 14 22[a] | 8 57 |
| Average Daily Dry Feed[A,D] Consumption[B] Per Calf During Period 18[C] (lbs) | 12 74[b] | 15 00[a] | 15 02[a] | 8 89 |
| Average Daily Dry Feed[A,D] Consumption[B] Per Calf During Period 19[C] (lbs) | 14 08[b] | 15 38[ab] | 16 40[a] | 8 53 |
| Average Daily Dry Feed[A,D] Consumption[B] Per Calf During Period 20[C] (lbs) | 14 84 | 14 78 | 16 41 | 12 35 |
| Average Daily Dry Feed[A,D] Consumption[B] Per Calf During Period 21[C] (lbs) | 14 23[b] | 16 57[a] | 16 99[a] | 4 44 |
| Average Daily Dry Feed[A,D] Consumption[B] Per Calf During Period 22[C] (lbs) | 15 04 | 15 91 | 16 18 | 7 27 |
| Average Daily Dry Feed[A,D] Consumption[B] Per Calf During Period 23[C] (lbs) | 15 37 | 16 49 | 16 76 | 6 00 |
| Average Daily Dry Feed[A,D] Consumption[B] Per Calf During Period 8 Thru Period 23[C] (lbs) | 10 40[b] | 11 40[ab] | 12 03[d] | 7 00 |

[A]Dry Feed for Control #1A was Total Calf Ration (texturized), 18% crude protein, with 90 g/ton lasalocid. Dry Feed for Control #1B & Psyllium Test #1 was Total Calf Ration (texturized), 28% crude protein, with 90 g/ton lasalocid
[B]Dry Feed Weight is provided on a dry matter (dm) basis
[C]Each period had a seven day duration
[D]Due to the bloating problems chopped grass hay was offered beginning week 15 at the rate of 0.5 lbs/calf/day. This was increased to 1 lb/calf/day for weeks 22 and 23
[a,b]Numbers within the same row with different single letter superscripts differ at a probability value of P < 0.05

These details of Table 9 demonstrate that the average daily dry animal feed consumption per calf during the post-weaning period increased by more than 15 percent for the calves of Psyllium Test #1 versus the calves of Control #1A, and increased by about 5.5 percent in the calves of Psyllium Test #1 versus the calves of Control #1B.

Finally, feed efficiency details during the sixteen individual weeks of the post-weaning period, over the entire post-weaning period, and over the combination of the pre-weaning period and the post-weaning period are provided in Table 10 below in terms of the feed/gain ratio, which is the inverse of feed efficiency:

TABLE 10

Feed Efficiency During Post-Weaning Period of Example 1

| | Control #1A[B] | Control #1B[C] | Psyllium Test #1[C] | Coefficient of Variation (C.V.) |
|---|---|---|---|---|
| Average Feed/Gain Ratio During Period 8[A] | 1 61 | 8.13 | 2.40 | 130 01 |
| Average Feed/Gain Ratio During Period 9[A] | 2.01 | 1.54 | 1 92 | 17 51 |
| Average Feed/Gain Ratio During Period 10[A] | 2.29 | 2 56 | 2.10 | 23 31 |
| Average Feed/Gain Ratio During Period 11[A] | 3.12 | 3.36 | 3 38 | 10 45 |
| Average Feed/Gain Ratio During Period 12[A] | 2.78 | 3.20 | 3 28 | 28.19 |
| Average Feed/Gain Ratio During Period 13[A] | 3.90 | 3.86 | 3 74 | 10 05 |
| Average Feed/Gain Ratio During Period 14[A] | 4.83 | 5.01 | 5 21 | 25 52 |
| Average Feed/Gain Ratio During Period 15[A] | 3.14 | 3 54 | 3.18 | 12 74 |
| Average Feed/Gain Ratio During Period 16[A] | 4 00 | 6.42 | 4 84 | 29 70 |
| Average Feed/Gain Ratio During Period 17[A] | 3.85 | 4 03 | 4 53 | 21 39 |
| Average Feed/Gain Ratio During Period 18[A] | 4 10 | 5.06 | 4 64 | 25 54 |
| Average Feed/Gain Ratio During Period 19[A] | 4.21 | 3.45 | 3 53 | 35 31 |
| Average Feed/Gain Ratio During Period 20[A] | 6 10 | 6 55 | 6 88 | 30 32 |
| Average Feed/Gain Ratio During Period 21[A] | 3.81 | 4.88 | 4 85 | 22 00 |
| Average Feed/Gain Ratio During Period 22[A] | 5.05 | 4 92 | 4 99 | 22 41 |
| Average Feed/Gain Ratio During Period 23[A] | 5 03 | 6 30 | 7 12 | 38 53 |
| Average Feed/Gain Ratio[D] During Period 8 Thru Period 23[A] | 3 61[b] | 4.04[a] | 3 92[a] | 4 58 |
| Average Feed/Gain Ratio[D] During Period 1 Thru Period 23[A] | 3.95 | 4.07 | 4 05 | 3 92 |

[A]Each period had a seven day duration
[B]Dry Feed for Control #1A during Periods 8–23 was Total Calf Ration (texturized), 18% crude protein, with 90 g/ton lasalocid
[C]Dry Feed for Control #1B & Psyllium Test #1 during Periods 8–23 was Total Calf Ration (texturized), 28% crude protein, with 90 g/ton lasalocid
[D]The Feed/Gain Ratio Average is a ratio of the weight of feed consumed per weight gained. The Feed/Gain Ratio Average During Periods 8–23 is the mean of all Feed/Gain Ratio Averages during each of the individual periods (8–23) for each individual calf
[E]The Feed/Gain Ratio Average is a ratio of the weight of feed consumed per weight gained. The Feed/Gain Ratio Average During Periods 1–23 is the mean of all Feed/Gain Ratio Averages during each of the individual periods (1–23) for each individual calf
[a,b]Numbers within the same row with different single letter superscripts differ at a probability value of P < 0.05

The details provided in Table 10 above illustrate that the Feed/Gain Ratio average during the post-weaning period decreased from 4.04 for the calves of Control #1B to 3.92 for the calves of Psyllium Test #1, which represents approximately a 3 percent Feed/Gain Ratio improvement by the calves of Psyllium Test #1 versus the calves of Control #1B over the sixteen weeks of the post-weaning period. Conversely, since the Feed Efficiency is merely the inverse of the Feed/Gain Ratio, the details of Table 10 demonstrate that the calves of Psyllium Test #1 saw an increase of Feed Efficiency of about 3 percent, versus the Feed Efficiency of the calves of Control #1B.

Example 2

This example demonstrates the effect of feeding young calves, during the pre-weaning period, calf milk replacer at an enhanced rate of about 2.50 pounds of calf milk replacer per day, on a dry weight basis, along with a psyllium composition. In this example, seventy-two (72) Holstein bull calves from California ranging in age from 3 to 10 days old and averaging about 102 pounds each, with a range of about 89 to about 114 pounds each, were assigned to one of three different treatments. A first treatment is referred to herein as "Control #2A", a second treatment is referred to herein as "Control #2B", and a third treatment is referred to herein as "Psyllium Test #2".

Each calf was tested for gamma globulin and assigned to gamma globulin level (1), (2), (3), (4), or (5), as described in Example 1. Equal numbers of calves from each of the different level (1), (2), (3), (4), and (5) gamma globulin concentration ranges, as in Example 1, were placed in the three different treatments (Control #2A, Control #2B and Psyllium Test #2).

The calves from the three different treatments were each fed and monitored during both the pre-weaning period and the post-weaning period. Details about the pre-weaning period handling and feed consumption for the calves of these three different treatments are provided in Tables 11–17 below, while details about the handling and feed consumption of the calves during the post-weaning period are provided in Tables 17–20 below. In Example 2, the pre-weaning period and the post-weaning period, collectively, spanned a total of 23 weeks for the calves of Control #2A, Control #2B and Psyllium Test #2. The pre-weaning period lasted seven weeks, and the post-weaning period lasted sixteen weeks, though the calves of Control #2A were generally only fed the fluid animal feed through the sixth week of the pre-weaning period.

During the pre-weaning period, each of the calves of the three different treatments had continuing and equal access to a calf starter that is referred to in Table 11 below as "total calf ration." Also, during the pre-weaning period, each calf of each treatment had continuing and equal access to fresh water, ad libitum. The total calf ration fed to the calves of Control #2A, Control #2B, and Psyllium Test #2 during the pre-weaning period of Example 2 was the same as the total calf ration that was fed to the calves of Control #1A, Control #1B, and Psyllium Test #1, respectively, during the pre-weaning period of Example 1, with the exception that the total calf ration fed to the calves of Control #2A, Control #2B, and Psyllium Test #2 during the pre-weaning period was texturized rather than pelleted. The calves of the three different treatments each received calf milk replacer during the pre-weaning period. The calf milk replacer fed to the calves of Control #2A, Control #2B, and Psyllium Test #2 was the same as the calf milk replacer fed to the calves 1 of Control #1A, Control #1B, and Psyllium Test #1, respectively, in Example 1.

The calf milk replacer was fed to the calves of Control #2A in two equal feedings at an overall rate of about 1.25 pounds of calf milk replacer per calf per day (about 0.625 pounds of calf milk replacer per calf per feeding of calf milk replacer), based upon the dry weight of the calf milk replacer. The calf milk replacer was fed to the calves of Control #2B and the calves of Psyllium Test #2 in two equal feedings at an overall rate of about 2.50 pounds of calf milk replacer per calf per day (about 1.25 pounds of calf milk replacer per calf per feeding of calf milk replacer), based upon the dry weight of the calf milk replacer. Thus, the calf milk replacer was fed to the calves of Control #2B and the calves of Psyllium Test #2 at the "enhanced feeding rate" for the calf milk replacer, and the calf milk replacer was fed to the calves of Control #2A at the "conventional feeding rate" for the calf milk replacer.

In Example 2, the calves of Control #2A and of Control #2B did not receive any of the psyllium composition during the pre-weaning period or, for that matter, during the post-weaning period. On the other hand, the calves of Psyllium Test #2 received about 6.24 grams of psyllium composition per calf per calf milk replacer feeding, or about 12.48 grams of psyllium composition per calf per day, during the pre-weaning period. Details about combination of the psyllium composition (for Psyllium Test #1 only) with the powdered milk replacer; rehydration of the powdered milk replacer to form the rehydrated milk replacer (or fluid milk replacer); and combination of the antibiotic blend, and the rehydrated milk replacer (or fluid milk replacer) to form the fluid animal feed are the same as those provided in Example 1.

The psyllium composition fed to the calves of Psyllium Test #2 had a purity of about 98 weight percent, based upon the total weight of the psyllium composition, which means that the psyllium composition contained about 98 weight percent and also included about 2 weight percent of light extraneous matter and/or heavy extraneous matter psyllium, based upon the total weight of the psyllium composition. The psyllium composition was milled to allow 100 percent of the psyllium composition to pass through a Bureau of Standards Sieve Number 100 mesh screen from the U.S. Standard Sieve Series. The swell volume of the psyllium composition ranged from about 74.2 milliliters of water per gram of the psyllium composition to about 103.7 milliliters of water per gram of the psyllium composition, with an average swell volume of about 86.3 milliliters of water per gram of the psyllium composition.

The fluid animal feed fed to the calves of Control #2A and Control #2B included the rehydrated milk replacer (also referred to herein as the fluid milk replacer), along with a small amount of antibiotics, but did not contain any of the psyllium composition. The fluid animal feed fed to the calves of Psyllium Test #2 included the rehydrated milk replacer, a small amount of the antibiotics, and the psyllium composition. The antibiotics used for the calves of Control #2A, Control #2B, and Psyllium Test #2 consisted of a blend of Neomycin and Oxytetracycline. Details about the concentrations of the Neomycin and Oxytetracycline employed for the calves of Control #2A, Control #2B, and Psyllium Test #2 are the same as those described in Example 1 for the calves of Control #1A, Control #1B, and Psyllium Test #1, respectively. The antibiotic blend was added at a different concentration to the fluid animal feed that was fed to the calves of Control #2A versus the concentration of antibiotic added to the fluid animal feed that was fed to the calves of Control #2B and Psyllium Test #2 to cause each calf in each of the three different treatments to receive the same daily dosage of each of the antibiotics of the antibiotic blend.

The fluid animal feed was individually fed to each of the calves in each of the three different treatments twice per day at about 7:00 a.m. and again at about 4:15 p.m. Each of the calves of each of the treatments quickly consumed all of their particular allotment of the fluid animal feed within a few minutes of being provided with the fluid animal feed. On the other hand, the calves of each of the three different treatments were, as previously indicated, given continuous and equal access to dry animal feed (the total calf ration) and fresh water. Furthermore, each test calf in the three different treatments received veterinary care and management consistent with appropriate recommendations in the *Guide for the Care and Use of Agriculttiral Animals in Agricultural Research and Teaching.* (1st Edition, March 1988).

All calves in the three different treatments were fully weaned from the fluid animal feed by the end of the seventh week of the pre-weaning period. The fluid animal feed was generally withdrawn from the calves of Control #2A at the end of the sixth week of the pre-weaning period, whereas the fluid animal feed was generally withdrawn from the calves of Control #2B and Psyllium Test #2 at the end of the seventh week of the pre-weaning period, though the calves of the Control #2B and Psyllium Test #2 only received one feeding of the fluid animal feed per day (about 1.25 pounds of calf milk replacer per calf per feeding of calf milk replacer, based upon the dry weight of the calf milk replacer) during the seventh week of the pre-weaning period.

Details about the diets of the calves during the pre-weaning period and details about the calf milk replacer component of the fluid animal feed for the three different treatments are provided in Tables 11 and 12 below:

TABLE 11

Diet During Pre-Weaning Period of Example 2

| Treatment Name | Milk Replacer (MR) Description | Total Calf Ration (TCR) | Number of Calves |
|---|---|---|---|
| Control #2A | 22:20 All Milk[A], 1.25#/calf/day[B] | Yes[C] | 24 |
| Control #2B | 28:20 All Milk[D], 2.5#/calf/day[E] | Yes[F] | 24 |
| Psyllium Test #2 | 28:20 All Milk[D], 2.5#/calf/day[E] w/Psyllium[G] | Yes[F] | 24 |

[A]NT 400 200 (Neomycin/Oxytetracycline @ 400/200 grams/ton)
[B]Calves were weaned at 6 weeks provided they were eating over 1 0 pound of Total Calf Ration per day. Starting at week 8, calves were moved to a nearby facility. The trial was terminated after 23 weeks on test.
[C]Total Calf Ration (texturized), 18% crude protein, with 90 g/ton lasalocid.
[D]NT 200:100 (Neomycin/Oxytetracycline @ 200/100 grams/ton)
[E]Calves were fed in the a.m. only (1 25#/calf/day) during week 7. Starting at week 8, calves were weaned & moved to a nearby facility.
[F]Total Calf Ration (pelleted), 26% crude protein, with 90 g/ton lasalocid
[G]Hand added at 6 24 g/calf/feeding Psyllium had a purity of 98% and was milled so that 100% passed through a Bureau of Standards Sieve Number 100 mesh screen from the U.S. Standard Sieve Series. Swell volumes ranged from 74 2–103 7 mil/gm (x = 86 3 ml/gm)

Next, details about the average weight gain per calf during the seven individual weeks of the pre-weaning period along with an average total weight gain per calf over the entire pre-weaning period are provided in Table 13 below:

TABLE 13

Weight Gain During Pre-Weaning Period of Example 2

| | Control #2A | Control #2B | Psyllium Test #2 | Coefficient of Variation (C.V.) |
|---|---|---|---|---|
| Average Gain Per Calf During Period 1[A] (lbs) | −0.81[b] | 4.14[a] | 4.50[a] | 668.51 |
| Average Gain Per Calf During Period 2[A] (lbs) | 1.61 | 5.08 | 5.27 | 182.17 |
| Average Gain Per Calf During Period 3[A] (lbs) | 9.31[b] | 14.62[a] | 13.30[a] | 47.46 |
| Average Gain Per Calf During Period 4[A] (lbs) | 9.13[b] | 11.85[a] | 12.63[a] | 30.88 |
| Average Gain Per Calf During Period 5[A] (lbs) | 9.04[b] | 12.43[a] | 11.96[a] | 35.45 |
| Average Gain Per Calf During Period 6[A] (lbs) | 8.34 | 11.21 | 12.04 | 49.23 |
| Average Gain Per Calf During Period 7[A] (lbs) | 5.80[b] | 12.12[a] | 9.98[ab] | 79.87 |
| Average Total Gain Per Calf During Period 1 Through Period 7 (lbs) | 42.42[b] | 71.46[a] | 69.68[a] | 27.85 |

[A]Each period had a seven day duration.
[a,b]Numbers within the same row with different single letter superscripts differ at a probability value of $P < 0.05$ The details of Table 13 demonstrate an increase of more than 64 percent in the average total weight gain per calf over the entire pre-weaning period for the calves of Psyllium Test #2 versus the calves of Control #2A.

Next, details about the average milk replacer consumption per calf during the seven individual weeks of the pre-weaning period and over the entire pre-weaning period are provided in Table 14 below:

TABLE 12

Milk Replacer Feeding Details During Pre-Weaning Period of Example 2

| | Description | Control #2A | Control #2B | Psyllium Test #2 |
|---|---|---|---|---|
| | Weight Percent Milk Replacer Powder In Fluid Milk Replacer[a] | 13 51 | 17 24 | 17 24 |
| Milk Replacer Fed Twice Daily (Period 1 Thru Period 6)[C] | Pounds of Milk Replacer Powder Per Milk Replacer Feeding[A] | 0 625 | 1 25 | 1 25 |
| | Pounds of Water Per Milk Replacer Feeding[A] | 4 00 | 6 00 | 6 00 |
| | Pounds of Fluid Milk Replacer Per Milk Replacer Feeding[A] | 4 625 | 7 25 | 7 25 |
| Total Pounds of Milk Replacer Powder Fed During Periods 1–6 (On a Dry Matter Basis) | | 52 5 | 105 0 | 105 0 |
| Milk Replacer Fed Once Daily (Period 7)[C] | Pounds of Milk Replacer Powder Per Milk Replacer Feeding[B] | 0 0 | 1 25 | 1 25 |
| | Pounds of Water Per Milk Replacer Feeding[B] | 0 0 | 6 00 | 6 00 |
| | Pounds of Fluid Milk Replacer Per Milk Replacer Feeding[B] | 0 0 | 7 25 | 7 25 |
| Total Pounds of Milk Replacer Powder Fed During Period 7 (on a Dry Matter Basis) | | 0 0 | 8 75 | 8 75 |
| Total Pounds of Milk Replacer Powder Fed During Periods 1–7 (on a Dry Matter Basis) | | 52 5 | 113 75 | 113 75 |

[A]Two Feedings of Milk Replacer Per Day For Control #2A, Control #2B, and Psyllium Test #2 During Period 1 Thru Period 6
[B]One Feeding of Milk Replacer Per Day For Control #2B & Psyllium Test #2 During Period 7, No feedings of Milk Replacer For Control #2A During Period 7
[C]Each period had a seven day duration
[a]Based on the total weight of the Fluid Milk Replacer

TABLE 14

Milk Replacer Consumption During Pre-Weaning Period of Example 2

|  | Control #2A | Control #2B | Psyllium Test #2 | Coefficient of Variation (C V) |
|---|---|---|---|---|
| Average Milk Replacer Consumption[A] Per Calf During Period 1[B] (lbs) | 7.34[b] | 11.83[a] | 12.26[a] | 18 96 |
| Average Milk Replacer Consumption[A] Per Calf During Period 2[B] (lbs) | 8 52[b] | 11.52[a] | 11.35[a] | 18.04 |
| Average Milk Replacer Consumption[A] Per Calf During Period 3[B] (lbs) | 8 67[b] | 16.17[a] | 15.81[a] | 11 94 |
| Average Milk Replacer Consumption[A] Per Calf During Period 4[B] (lbs) | 8 79[c] | 17 18[a] | 16.75[ab] | 8.54 |
| Average Milk Replacer Consumption[A] Per Calf During Period 5[B] (lbs) | 8 79[b] | 17 19[a] | 17 25[a] | 7 40 |
| Average Milk Replacer Consumption[A] Per Calf During Period 6[B] (lbs) | 8.77[b] | 17.32[a] | 17.29[a] | 6 07 |
| Average Milk Replacer Consumption[A] Per Calf During Period 7[B] (lbs) | 0 11[b] | 8.75[a] | 8.76[a] | 14 67 |
| Average Total Milk Replacer Consumption[A] Per Calf During Period 1 Through Period 7 (lbs) | 50.98[b] | 99.97[a] | 99.46[a] | 7.00 |

[A]Milk Replacer Component Weight is provided on a dry matter (dm) basis
[B]Each period had a seven day duration
[a,b,c]Numbers within the same row with different single letter superscripts differ at a probability value of $P < 0.05$ Next, details about the average amount of dry feed consumption during the seven individual weeks of the pre-weaning period and over the entire pre-weaning period are provided in Table 15 below:

TABLE 15

Dry Feed Consumption During Pre-Weaning Period of Example 2

|  | Control #2A | Control #2B | Psyllium Test #2 | Coefficient of Variation (C V.) |
|---|---|---|---|---|
| Average Dry Feed[A] Consumption[B] Per Calf During Period 1[C] (lbs) | 0 11 | −0.13 | −0.11 | 2409.44 |
| Average Dry Feed[A] Consumption[B] Per Calf During Period 2[C] (lbs) | 1 06 | 0 79 | 0 34 | 160 04 |
| Average Dry Feed[A] Consumption[B] Per Calf During Period 3[C] (lbs) | 4 81[a] | 1.88[b] | 1.69[b] | 71.31 |
| Average Dry Feed[A] Consumption[B] Per Calf During Period 4[C] (lbs) | 6 89[a] | 3.15 | 2.91[b] | 54.60 |
| Average Dry Feed[A] Consumption[B] Per Calf During Period 5[C] (lbs) | 8.48[a] | 3 75[b] | 3.53[b] | 49.75 |
| Average Dry Feed[A] Consumption[B] Per Calf During Period 6[C] (lbs) | 9.74[a] | 4 87 | 4.18[b] | 48.92 |
| Average Dry Feed[A] Consumption[B] Per Calf During Period 7[C] (lbs) | 18 55[a] | 14 02[b] | 11 73[b] | 35.57 |
| Average Total Dry Feed[A] Consumption[B] Per Calf During Period 1 Through Period 7 (lbs) | 49 64[a] | 28.33[b] | 24.27[b] | 43.28 |

[A]Dry Feed for Control #2A was Total Calf Ration (texturized), 18% crude protein, with 90 g/ton lasalocid; Dry Feed for Control #2B & Psyllium Test #2 was Total Calf Ration (texturized), 26% crude protein, with 90 g/ton lasalocid
[B]Dry Feed Weight is provided on a dry matter (dm) basis
[C]Each period had a seven day duration.
[a,b]Numbers within the same row with different single letter superscripts differ at a probability value of $P < 0.05$ Next, weight, weight gain, and feed efficiency details during the pre-weaning period are provided in Table 16 below:

TABLE 16

Feed Efficiency During Pre-Weaning Period of Example 2

|  | Control #2A | Control #2B | Psyllium Test #2 | Coefficient of Variation (C.V.) |
|---|---|---|---|---|
| Average Initial Ig[A] For All Calves | 2 64 | 2.33 | 2.83 | 51.70 |
| Average[B] Initial Weight Per Calf, lbs. (at start of period 1) | 101 9 | 101.9 | 101.9 |  |
| Average[C] Ending Weight Per calf, lbs. (at end of period 7) | 144 7[b] | 171.6[a] | 175.2[a] | 2.49 |

TABLE 16-continued

Feed Efficiency During Pre-Weaning Period of Example 2

| | Control #2A | Control #2B | Psyllium Test #2 | Coefficient of Variation (C.V.) |
|---|---|---|---|---|
| Average[D] Total Gain Per Calf During Period 1 Through Period 7 (lbs) | 42 42[b] | 71 46[a] | 69.68[a] | 27.85 |
| Feed Efficiency Average[E] During Period 1 Thru Period 7 | 0 386 | 0 549 | 0.568 | 54.81 |

[A]Expressed in weight percent, as measured by Zinc Sulfate Turbidity test then assigned to level 1, level 2, level 3, level 4, or level 5 as follows (1) Ig = 0 00–0 49, (2) Ig = 0 50–0 99, (3) Ig = 1 00–1 49, (4) Ig = 1 50–2 49, (5) Ig = 2 5 and higher.
[B]The initial weight(s) of calves that were present in period 1 but did not complete period 7 are not included in this average.
[C]This average excludes calves that were present in period 1 but did not complete period 7
[D]This average will not necessarily equal the value obtained by subtracting the average initial weight per calf (at start of period 1) from the average ending weight per calf (at the end of period 7), since this average is the sum of the weekly average gains per calf for periods 1–7 which may include one or more calves that did not finish period 7
[E]The Feed Efficiency Average is a ratio of the weight of feed consumed verses the weight gained The Feed Efficiency Average During Periods 1–7 is the mean of all Feed Efficiency Averages during each of the individual periods (1–7) for each individual calf.
[a,b]Numbers within the same row with different single letter superscripts differ at a probability value of $P < 0\ 05$ These details of Table 16 demonstrate an increase of the feed efficiency average over the entire pre-weaning period from 0.386 for the calves of Control #2A to 0.568 for the calves of Psyllium Test #2, which indicates that feed efficiency increased by about 47 percent for the calves of Psyllium Test #2 versus the calves of Control #2A.

Next, details about average calf weights during the pre-weaning and post-weaning periods of Example 2 are provided in Table 17 below:

Tables 18 through 20 that are provided below present details about weight gain, feed consumption, and feed efficiency during the sixteen weeks of the post-weaning period and also present data on the weight gain and the feed efficiency over the entire twenty-three week composite of the pre-weaning period and the post-weaning period. During the post-weaning period, none of the calves of any of the three testing regimens received any of the fluid animal feed

TABLE 17

Average Calf Weights During Pre- and Post-Weaning Periods of Example 2

| | Control #2A | Control #2B | Psyllium Test #2 | Coefficient of (C.V.) |
|---|---|---|---|---|
| Average[A] Weight Per Calf at Start of Period 1 (pounds) | 101 2 | 102.0 | 102.0 | 1.35 |
| Average[A] Weight Per Calf at Start of Period 8 and End of Period 7 (pounds) | 144 7[b] | 171.6[a] | 175.2[a] | 2.49 |
| Average[B] Weight Per Calf at End of Period 23 (pounds) | 471 3[b] | 495 6[ab] | 518.6[a] | 4.91 |

[A]This average excludes calves that were present in period 1 but did not complete period 7
[B]This average excludes calves that were present in period 8 but did not complete period 23
[a,b]Numbers within the same row with different single letter superscripts differ at a probability value of $P < 0.05$ (and thus did not receive any of the calf milk replacer) or any of the psyllium composition.

Also, during the post-weaning period, the calves of each of the three testing regimens had equal access to the total calf ration that served as the dry animal feed. The total calf ration of the post-weaning period was the same as the total calf ration of the pre-weaning period for the calves of Control #2A, Control #2B and Psyllium Test #2. Also, the calves of Control #2A, Control #2B, and Psyllium Test #2 had continuous and equal access to fresh water ad libitumn during the post-weaning period. Finally, starting with week fifteen (week 8 of the post-weaning period), chopped grass hay was offered at a low rate to the calves of the three different treatments to address digestion issues, such as the potential for bloating.

Weight gain details for the sixteen different weeks of the post-weaning period, over the entire post-weaning period, and over the composite of the pre-weaning and post-weaning periods are provided in Table 18 below:

TABLE 18

Weight Gain During Post-Weaning Period of Example 2

| Period[A] | | Control #2A[B] | Control #2B[C] | Psyllium Test #2[C] | Coefficient of Variation (C.V) |
|---|---|---|---|---|---|
| 8[A] | Average Daily Gain Per Calf (lbs) | 3 02[a] | 2.04[b] | 1.97[b] | 11 17 |
| | Average Total Gain Per Calf During Period (lbs) | 21.13[a] | 14 28[b] | 13 78[b] | |
| 9[A] | Average Daily Gain Per Calf (lbs) | 2.17[b] | 2.25[ab] | 2 71[a] | 11.44 |
| | Average Total Gain Per Calf During Period (lbs) | 15 20[b] | 15.73[ab] | 18 95[a] | |
| 10[A] | Average Daily Gain Per Calf (lbs) | 1.95 | 2.26 | 2 88 | 39.60 |
| | Average Total Gain Per Calf During Period (lbs) | 13 63 | 15 80 | 20 15 | |
| 11[A] | Average Daily Gain Per Calf (lbs) | 2.34[y] | 2 31[y] | 3 26[x] | 21.53 |
| | Average Total Gain Per Calf During Period (lbs) | 16 35[y] | 16.18[y] | 22 83[x] | |
| 12[A] | Average Daily Gain Per Calf (lbs) | 2.05[y] | 2 87[x] | 2 39[xy] | 21.69 |
| | Average Total Gain Per Calf During Period (lbs) | 14 35[y] | 20 10[x] | 16 73[xy] | |
| 13[A] | Average Daily Gain Per Calf (lbs) | 2.54[y] | 2.96[xy] | 3 12[x] | 14.05 |
| | Average Total Gain Per Calf During Period (lbs) | 17 80[y] | 20.70[xy] | 21 85[x] | |
| 14[A] | Average Daily Gain Per Calf (lbs) | 2.97[y] | 3.53[x] | 3.59[x] | 10 68 |
| | Average Total Gain Per Calf During Period (lbs) | 20 80[y] | 24.70[x] | 25 13[x] | |
| 15[A] | Average Daily Gain Per Calf (lbs) | 3.15 | 2.38 | 2.84 | 29.22 |
| | Average Total Gain Per Calf During Period (lbs) | 22.03 | 16.65 | 19 90 | |
| 16[A] | Average Daily Gain Per Calf (lbs) | 3.51 | 3.34 | 3 31 | 15 52 |
| | Average Total Gain Per Calf During Period (lbs) | 24 58 | 23 38 | 23 18 | |
| 17[A] | Average Daily Gain Per Calf (lbs) | 3.55 | 2 91 | 3 17 | 26 62 |
| | Average Total Gain Per Calf During Period (lbs) | 24 85 | 20.40 | 22.20 | |
| 18[A] | Average Daily Gain Per Calf (lbs) | 2 97[xy] | 3.56[x] | 2 64[y] | 21 56 |
| | Average Total Gain Per Calf During Period (lbs) | 20.78[xy] | 24 90[x] | 18 45[y] | |
| 19[A] | Average Daily Gain Per Calf (lbs) | 3.59 | 3 50 | 3 20 | 26 26 |
| | Average Total Gain Per Calf During Period (lbs) | 25 15 | 24 47 | 22 40 | |
| 20[A] | Average Daily Gain Per Calf (lbs) | 2.05[y] | 2 45[xy] | 3 24[x] | 30 81 |
| | Average Total Gain Per Calf During Period (lbs) | 14 38[y] | 17.15[xy] | 22 70[x] | |
| 21[A] | Average Daily Gain Per Calf (lbs) | 2 33 | 2 15 | 1 73 | 29 70 |
| | Average Total Gain Per Calf During Period (lbs) | 16 28 | 15 10 | 12 10 | |
| 22[A] | Average Daily Gain Per Calf (lbs) | 4 71 | 4.59 | 4 23 | 20 20 |
| | Average Total Gain Per Calf During Period (lbs) | 32 98 | 32 13 | 29 57 | |
| 23[A] | Average Daily Gain Per Calf (lbs) | 3.76[xy] | 3 19[y] | 4 79[x] | 27 27 |
| | Average Total Gain Per Calf During Period (lbs) | 26 33[xy] | 22.35[y] | 33.50[x] | |
| 8–23[A] | Average[D] Daily Gain Per Calf During Period 8 thru Period 23 (lbs) | 2.92 | 2.89* | 3 07* | 6 63 |
| | Average[E] Total Gain Per Calf During Period 8 thru Period 23 (lbs) | 326.58 | 324.00* | 343.40* | |
| 1–23[A] | Average[F] Daily Gain Per Calf During Period 1 thru Period 23 (lbs) | 2.30[b] | 2.44[ab]** | 2 59[d]** | 6 33 |
| | Average[G] Total Gain Per Calf During Period 1 thru Period 23 (lbs) | 370 03[b] | 393.60[ab]** | 416 65[d]** | |

[A]Each period had a seven day duration
[B]Dry Feed for Control #2A during Periods 8–23 was Total Calf Ration (texturized), 18% crude protein, with 90 g/ton lasalocid
[C]Dry Feed for Control #2B & Psyllium Test #2 during Periods 8–23 was Total Calf Ration (texturized), 26% crude protein, with 90 g/ton lasalocid
[D]This average was calculated by dividing the Average Total Gain Per Day During Period 8 thru Period 23 by 112 (7 × 16)
[E]This average will not necessarily equal the value obtained by subtracting the average initial weight per calf (at start of period 8) from the average ending weight per calf (at the end of period 23), since this average is the sum of the weekly average gains per calf for periods 8–23 which may include one or more calves that did not finish period 23
[F]This average was calculated by dividing the Average Total Gain Per Day During Period 1 thru Period 23 by 161 (7 × 23)
[G]This average will not necessarily equal the value obtained by subtracting the average initial weight per calf (at start of period 1) from the average ending weight per calf (at the end of period 23), since this average is the sum of the weekly average gains per calf for periods 1–23 which may include one or more calves that did not finish period 23
[a,b]Numbers within the same row with different single letter superscripts differ at a probability value of P < 0.05
[x,y]Numbers within the same row with different single letter superscripts differ at a probability value of P < 0.10
*Numbers within the same row with similar superscripts have a probability value P = 0.2581
**Numbers within the same row with similar superscripts have a probability value P = 0.2385

The details that are provided in Table 18 demonstrate that the average total weight gain per calf during the entire post-weaning period increased by about 5.15 percent for the calves of Psyllium Test #2 versus the calves of Control #2A and increased by nearly 6 percent for the calves of Psyllium Test #2 versus the calves of Control #2B. Also, the details of Table 18 illustrate that the average total gain per calf over the 23 weeks of the pre-weaning period and the post-weaning period increased by about 12.6 percent for the calves of Psyllium Test #2 versus the calves of Control #2A and increased by nearly 6 percent for the calves of Psyllium Test #2 versus the calves of Control #2B.

Next, details about the dry animal feed (total calf ration) consumption during the sixteen individual weeks of the post-weaning period and over the entire post-weaning period are provided in Table 19 below:

TABLE 19

Dry Feed Consumption During Post-Weaning Period of Example 2

|  | Control #2A | Control #2B | Psyllium Test #2 | Coefficient of (C.V.) |
|---|---|---|---|---|
| Average Daily Dry Feed[A] Consumption[B] Per Calf During Period 8[C] (lbs) | 4 73 | 4 56 | 4 50 | 7 19 |
| Average Daily Dry Feed[A] Consumption[B] Per Calf During Period 9[C] (lbs) | 6 66 | 6 47 | 6 81 | 7.91 |
| Average Daily Dry Feed[A] Consumption[B] Per Calf During Period 10[C] (lbs) | 7 37 | 6 88 | 8 26 | 14 65 |
| Average Daily Dry Feed[A] Consumption[B] Per Calf During Period 11[C] (lbs) | 7 45 | 7 08 | 8 42 | 13.03 |
| Average Daily Dry Feed[A] Consumption[B] Per Calf During Period 12[C] (lbs) | 8 28 | 8 45 | 9 78 | 13 78 |
| Average Daily Dry Feed[A] Consumption[B] Per Calf During Period 13[C] (lbs) | 9 75$^b$ | 10 54$^{ab}$ | 11 26$^a$ | 5 76 |
| Average Daily Dry Feed[A] Consumption[B] Per Calf During Period 14[C] (lbs) | 10 76$^b$ | 12 14$^a$ | 12 90$^a$ | 6 27 |
| Average Daily Dry Feed[A] Consumption[B] Per Calf During Period 15[C] (lbs) | 12 09$^b$ | 12 77$^b$ | 14 21$^a$ | 5.75 |
| Average Daily Dry Feed[A] Consumption[B] Per Calf During Period 16[C] (lbs) | 13 12$^y$ | 13 80$^{xy}$ | 14 91$^x$ | 7 69 |
| Average Daily Dry Feed[A] Consumption[B] Per Calf During Period 17[C] (lbs) | 13 91 | 14 59 | 15 70 | 10 49 |
| Average Daily Dry Feed[A] Consumption[B] Per Calf During Period 18[C] (lbs) | 16 57 | 16 54 | 16 82 | 7.41 |
| Average Daily Dry Feed[A] Consumption[B] Per Calf During Period 19[C] (lbs) | 15 42 | 16 04 | 15 84 | 9 56 |
| Average Daily Dry Feed[A] Consumption[B] Per Calf During Period 20[C] (lbs) | 17 08 | 17 25 | 17 72 | 13 57 |
| Average Daily Dry Feed[A] Consumption[B] Per Calf During Period 21[C] (lbs) | 17 56$^y$ | 17 45$^y$ | 19 34$^x$ | 7 12 |
| Average Daily Dry Feed[A] Consumption[B] Per Calf During Period 22[C] (lbs) | 18 63 | 18 05 | 19 12 | 9 64 |
| Average Daily Dry Feed[A] Consumption[B] Per Calf During Period 23[C] (lbs) | 19 93 | 19 55 | 21 33 | 9 55 |
| Average Daily Dry Feed[A] Consumption[B] Per Calf During Period 8 Thru Period 23[c] (lbs) | 12 46 | 12 63* | 13 56* | 6 67 |

[A]Dry Feed for Control #2A was Total Calf Ration (texturized), 18% crude protein, with 90 g/ton lasalocid. Dry Feed for Control #2B & Psyllium Test #2 was Total Calf Ration (texturized), 26% crude protein, with 90 g/ton lasalocid
[B]Dry Feed Weight is provided on a dry matter (dm) basis
[C]Each period had a seven day duration.
[a,b]Numbers within the same row with different single letter superscripts differ at a probability value of $P < 0\ 05$
[x,y]Numbers within the same row with different single letter superscripts differ at a probability value of $P < 0\ 10$
*Numbers within the same row with similar superscripts have a probability value $P = 0\ 1798$ The details of Table 19 demonstrate that the average daily dry animal feed consumption over the entire sixteen weeks of the post-weaning period increased by about 8.8 percent for the calves of Psyllium Test #2 versus the calves of Control #2A and increased by more than seven percent for the calves of Psyllium Test #2 versus the calves of Control #2B.

Finally, feed efficiency details during the sixteen individual weeks of the post-weaning period and over the entire post-weaning period, expressed in terms of the feed/gain ratio, which is the inverse of feed efficiency, are provided in Table 20 below:

TABLE 20

Feed Efficiency During Post-Weaning Period of Example 2

|  | Control #2A[B] | Control #2[C] | Psyllium Test #2[C] | Coefficient of Variation (C.V.) |
|---|---|---|---|---|
| Average Feed/Gain Ratio During Period 8[A] | 1 57$^a$ | 2.24$^{ab}$ | 2 34$^b$ | 9.44 |
| Average Feed/Gain Ratio During Period 9[A] | 3 15$^b$ | 2 89$^{ab}$ | 2.52$^a$ | 11.53 |
| Average Feed/Gain Ratio During Period 10[A] | 4 10 | 3 52 | 2 94 | 34.87 |
| Average Feed/Gain Ratio During Period 11[A] | 3.31$^y$ | 3 14$^{xy}$ | 2 59$^x$ | 17.02 |
| Average Feed/Gain Ratio During Period 12[A] | 4 34 | 2 95 | 4 28 | 33.11 |
| Average Feed/Gain Ratio During Period 13[A] | 3 91 | 3 60 | 3.60 | 13.78 |
| Average Feed/Gain Ratio During Period 14[A] | 3 71 | 3 45 | 3.65 | 15.03 |
| Average Feed/Gain Ratio During Period 15[A] | 4 53 | 5 43 | 5.03 | 24.98 |
| Average Feed/Gain Ratio During Period 16[A] | 3 92 | 4 15 | 4 55 | 13.47 |
| Average Feed/Gain Ratio During Period 17[A] | 4 13 | 5 04 | 5 35 | 27.22 |
| Average Feed/Gain Ratio During Period 18[A] | 6 55 | 4 77 | 6.40 | 32.13 |
| Average Feed/Gain Ratio During Period 19[A] | 4 35 | 4 89 | 5 85 | 31.47 |
| Average Feed/Gain Ratio During Period 20[A] | 9 55 | 7 37 | 5 61 | 44.33 |
| Average Feed/Gain Ratio During Period 21[A] | 8 53 | 8 47 | 21.11 | 99.79 |
| Average Feed/Gain Ratio During Period 22[A] | 4 02 | 3 94 | 4.77 | 24.21 |

TABLE 20-continued

Feed Efficiency During Post-Weaning Period of Example 2

|  | Control #2A[B] | Control #2[C] | Psyllium Test #2[C] | Coefficient of Variation (C.V.) |
|---|---|---|---|---|
| Average Feed/Gain Ratio During Period 23[A] | 5 29 | 6 60 | 4 58 | 26.89 |
| Average Feed/Gain Ratio During Period 8 Thru Period 23[A] | 4 26[a] | 4 37[ab] | 4.42[b] | 1.98 |

[A]Each period had a seven day duration
[B]Dry Feed for Control #2A during Periods 8–23 was Total Calf Ration (texturized), 18% crude protein, with 90 g/ton lasalocid
[C]Dry Feed for Control #2B & Psyllium Test #2 during Periods 8–23 was Total Calf Ration (texturized), 26% crude protein, with 90 g/ton lasalocid.
[D]The Feed/Gain Ratio Average is a ratio of the weight of feed consumed per weight gained The Feed/Gain Ratio Average During Periods 8–23 is the mean of all Feed/Gain Ratio Averages during each of the individual periods (8–23) for each individual calf
[a,b]Numbers within the same row with different single letter superscripts differ at a probability value of P < 0 05
[x,y]Numbers within the same row with different single letter superscripts differ at a probability value of P < 0 10

Although the present invention has been described with reference to preferred embodiments, workers skilled in the art will recognize that changes maybe made in form and detail without departing from the spirit and scope of the invention.

The invention claimed is:

1. A method of feeding ruminants, the method comprising: feeding a first ruminant a fluid animal feed composition during a pre-weaning feeding period, the fluid animal feed composition comprising a milk replacer and the first ruminant consuming about 1.25 pounds or more of the milk replacer per day, on a dry matter basis, during the pre-weaning feeding period; and feeding the first ruminant a supplemental feed material during the pre-weaning feeding period, the supplemental feed material comprising about 50 weight percent or more hemicellulose, based upon the dry weight of the supplemental feed material.

2. The method of claim 1 wherein the supplemental feed material is in powdered form.

3. The method of claim 1 wherein:

the method is effective to increase the feed efficiency of the first ruminant during a postweaning feeding period as compared to the feed efficiency of a second ruminant during the post-weaning feeding period; and feed provided to the second ruminant being free of the supplemental feed material, the second ruminant consuming about the same amount of the milk replacer, on a dry weight basis, during the pre-weaning feeding period as the first ruminant consumes during the pre-weaning feeding period.

4. The method of claim 3 wherein the first ruminant and the second ruminant are provided the same feed during the pre-weaning feeding period and during the post-weaning feeding period, with the exception that feed provided to the second ruminant is free of the supplemental feed material.

5. The method of claim 3 wherein feed provided to the first ruminant is free of the supplemental feed material during the post-weaning feeding period.

6. The method of claim 1 wherein:

the method is effective to increase the feed efficiency of the first ruminant during the preweaning feeding period as compared to the feed efficiency of a second ruminant during the pre-weaning feeding period; and feed provided to the second ruminant being free of the supplemental feed material, the second ruminant consuming about 1.25 pounds, or less, of the milk replacer per day, on a dry matter basis, during a first segment of the pre-weaning feeding period, and the first ruminant consuming more of the milk replacer per day during the first segment of the pre-weaning feeding period than the second ruminant may consume per day during the first segment of the pre-weaning feeding period, on a dry matter basis.

7. The method of claim 6 wherein the first ruminant consumes about 2.5 pounds or more of the milk replacer per day, on a dry matter basis, during the first segment of the pre-weaning feeding period.

8. The method of claim 6 wherein the first segment of the pre-weaning feeding period is about six weeks long.

9. The method of claim 6 wherein the method is effective to increase the feed efficiency of the first ruminant during the pre-weaning feeding period by about 30 percent or more, as compared to the feed efficiency of the second ruminant during the pre-weaning feeding period.

10. The method of claim 1 wherein:

the method is effective to increase feed consumption by the first ruminant during a postweaning feeding period as compared to feed consumption by a second ruminant during the post-weaning feeding period; and feed provided to the second ruminant free of the supplemental feed material, the second ruminant consuming about the same amount of the milk replacer, on a dry weight basis, during the pre-weaning feeding period as the first ruminant consumes during the pre-weaning feeding period.

11. The method of claim 1, the method further comprising providing the first ruminant with a dry animal feed composition during the pre-weaning feeding period, the method effective to cause the first ruminant to consume more of the dry animal feed composition during the pre-weaning feeding period than a second ruminant consumes during the pre-weaning feeding period, where the second ruminant is also provided with the dry animal feed composition during the pre-weaning feeding period, all feed provided to the second ruminant being free of the supplemental feed material.

12. The method of claim 11 wherein the second ruminant consumes about 1.25 pounds, or less, of the milk replacer per day, on a dry matter basis, during a first segment of the pre-weaning feeding period, the first ruminant consuming more of the milk replacer per day during the first segment of the pre-weaning feeding period than the second ruminant may consume per day during the first segment of the pre-weaning feeding period, on a dry matter basis, the milk replacer fed to the first ruminant having a greater concentration of protein than the milk replacer fed to the second ruminant, and the dry animal feed composition provided to the first ruminant having a greater concentration of protein than the dry animal feed composition provided to the second ruminant.

13. The method of claim 12 wherein the first ruminant consumes about 2.5 pounds or more of the milk replacer per day, on a dry matter basis, during the first segment of the pre-weaning feeding period.

14. The method of claim 12 wherein the first segment of the pre-weaning feeding period is about six weeks long.

15. The method of claim 1, the method further comprising providing the first ruminant with a dry animal feed composition during a post-weaning feeding period, the method effective to cause the first ruminant to consume more of the dry animal feed composition during the post-weaning feeding period than a second ruminant consumes during the post-weaning feeding period, where the second ruminant is also provided with the dry animal feed composition during the post-weaning feeding period, all feed provided to the second ruminant being free of the supplemental feed material.

16. The method of claim 13 wherein the second ruminant consumes about 1.25 pounds, or less, of the milk replacer per day, on a dry matter basis, during a first segment of the preweaning feeding period, the first ruminant consuming more of the milk replacer per day during the first segment of the pre-weaning feeding period than the second ruminant may consume per day during the first segment of the pre-weaning feeding period, on a dry matter basis, the milk replacer fed to the first ruminant having a greater concentration of protein than the milk replacer fed to the second ruminant, and the dry animal feed composition provided to the first ruminant having a greater concentration of protein than the dry animal feed composition provided to the second ruminant.

17. The method of claim 16 wherein the first ruminant consumes about 2.5 pounds or more of the milk replacer per day, on a dry matter basis, during the first segment of the pre-weaning feeding period.

18. The method of claim 16 wherein the first segment of the pre-weaning feeding period is about six weeks long.

19. The method of claim 1, the method further comprising providing the first ruminant with a dry animal feed composition during the pre-weaning feeding period, the method effective to cause the first ruminant to gain more weight during the pre-weaning feeding period than a second ruminant gains during the pre-weaning feeding period, where the second ruminant is also provided with the dry animal feed composition during the pre-weaning feeding period, all feed provided to the second ruminant during the pre-weaning feeding period being free of the supplemental feed material.

20. The method of claim 19 wherein the second ruminant consumes about 1.25 pounds, or less, of the milk replacer per day, on a dry matter basis, during a first segment of the pre-weaning feeding period, the first ruminant consuming more of the milk replacer per day during the first segment of the pre-weaning feeding period than the second ruminant may consume per day during the first segment of the pre-weaning feeding period, on a dry matter basis, the milk replacer fed to the first ruminant having a greater concentration of protein than the milk replacer fed to the second ruminant, and the dry animal feed composition provided to the first ruminant having a greater concentration of protein than the dry animal feed composition provided to the second ruminant.

21. The method of claim 20 wherein the first ruminant consumes about 2.5 pounds or more of the milk replacer per day, on a dry matter basis, during the first segment of the pre-weaning feeding period.

22. The method of claim 20 wherein the first segment of the pre-weaning feeding period is about six weeks long.

23. The method of claim 20 wherein the method is effective to cause the first ruminant to gain about 64% or more additional weight during the pre-weaning feeding period than the second ruminant gains during the pre-weaning feeding period.

24. The method of claim 1, the method further comprising providing the first ruminant with a dry animal feed composition during a post-weaning feeding period, the method effective to cause the first ruminant to gain more weight during the post-weaning feeding period than a second ruminant gains during the post-weaning feeding period, where the second ruminant is also provided with the dry animal feed composition during the post-weaning feeding period, all feed provided to the second ruminant during the pre-weaning feeding period being free of the supplemental feed material.

25. The method of claim 24 wherein the second ruminant consumes about 1.25 pounds, or less, of the milk replacer per day, on a dry matter basis, during a first segment of the pre-weaning feeding period, the first ruminant consuming more of the milk replacer per day during the first segment of the pre-weaning feeding period than the second ruminant may consume per day during the first segment of the pre-weaning feeding period, on a dry matter basis, the milk replacer fed to the first ruminant having a greater concentration of protein than the milk replacer fed to the second ruminant, and the dry animal feed composition provided to the first ruminant having a greater concentration of protein than the dry animal feed composition provided to the second ruminant.

26. The method of claim 25 wherein the first ruminant consumes about 2.5 pounds or more of the milk replacer per day, on a dry matter basis, during the first segment of the pre-weaning feeding period.

27. The method of claim 25 wherein the first segment of the pre-weaning feeding period is about six weeks long.

28. The method of claim 1 wherein:
the method is effective to increase the amount of weight gained by the first ruminant during a post-weaning feeding period as compared to the amount of weight gained by a second ruminant during the post-weaning feeding period; and
feed provided to the second ruminant being free of the supplemental feed material, the second ruminant consuming about the same amount of the milk replacer, on a dry weight basis, during the pre-weaning feeding period as the first ruminant consumes during the pre-weaning feeding period.

29. The method of claim 1, the method further comprising providing the first ruminant with a dry animal feed composition during a post-weaning feeding period, the method effective to cause the first ruminant to gain more weight during a composite feeding period than a second ruminant gains during the composite feeding period, where the second ruminant is also provided with the dry animal feed composition during the post-weaning feeding period, all feed provided to the second ruminant during the post-weaning feeding period being free of the supplemental feed material, and the composite feeding period comprising the pre-weaning feeding period and the post-weaning feeding period.

30. The method of claim 29 wherein the second ruminant consumes about 1.25 pounds, or less, of the milk replacer per day, on a dry matter basis, during a first segment of the pre-weaning feeding period, the first ruminant consuming more of the milk replacer per day during the first segment of the pre-weaning feeding period than the second ruminant may consume per day during the first segment of the pre-weaning feeding period, on a dry matter basis, the milk replacer fed to the first ruminant having a greater concentration of protein than the milk replacer fed to the second ruminant, and the dry animal feed composition provided to the first ruminant having a greater concentration of protein than the dry animal feed composition provided to the second ruminant.

31. The method of claim 30 wherein the first ruminant consumes about 2.5 pounds or more of the milk replacer per day, on a dry matter basis, during the first segment of the pre-weaning feeding period.

32. The method of claim 30 wherein the first segment of the pre-weaning feeding period is about six weeks long.

33. The method of claim 1 wherein:
the method is effective to increase the amount of weight gained by the first ruminant during a composite feeding period as compared to the amount of weight gained by a second ruminant during the composite feeding period, the composite feeding period comprising the pre-weaning feeding period and a post-weaning feeding period; and
feed provided to the second ruminant is free of the supplemental feed material, the second ruminant consuming-about the same amount of the milk replacer, on a dry weight basis, during the pre-weaning feeding period as the first ruminant consumes during the pre-weaning feeding period.

34. The method of claim 1 wherein the supplemental feed material comprises a psyllium composition.

35. A method of feeding ruminants, the method comprising:
feeding a first ruminant an effective amount of milk replacer during a pre-weaning feeding period; and
feeding the first ruminant about one to about thirty grams of a supplemental feed material during the pre-weaning feeding period, the supplemental feed material comprising hemicellulose, wherein:
the method is effective to increase the feed efficiency of the first ruminant during a post-weaning feeding period as compared to the feed efficiency of a second ruminant during the post-weaning feeding period; and
feed provided to the second ruminant is free of the supplemental feed material, the second ruminant consuming about the same amount of the milk replacer, on a dry weight basis, during the pre-weaning feeding period as the first ruminant consumes during the pre-weaning feeding period.

36. A method of feeding ruminants, the method comprising:
feeding a first ruminant an effective amount of milk replacer during a pre-weaning feeding period;
feeding the first ruminant about one to about thirty grams of a supplemental feed material during the pre-weaning feeding period, the supplemental feed material comprising hemicellulose; and
providing the first ruminant with a dry animal feed composition during a post-weaning feeding period, the method effective to cause the first ruminant to consume more of the dry animal feed composition during the post-weaning feeding period than a second ruminant consumes during the post-weaning feeding period, where the second ruminant is also provided with the dry animal feed composition during the post-weaning feeding period,
all feed provided to the second ruminant being free of the supplemental feed material.

37. The method of claim 36 wherein the second ruminant consumes about 1.25 pounds, or less, of the milk replacer per day, on a dry matter basis, during a first segment of the preweaning feeding period, the first ruminant consuming more of the milk replacer per day during the first segment of the pre-weaning feeding period than the second ruminant may consume per day during the first segment of the pre-weaning feeding period, on a dry matter basis, the milk replacer fed to the first ruminant having a greater concentration of protein than the milk replacer fed to the second ruminant, and the dry animal feed composition provided to the first ruminant having a greater concentration of protein than the dry animal feed composition provided to the second ruminant.

38. A method of feeding ruminants, the method comprising:
feeding a first ruminant an effective amount of milk replacer during a pre-weaning feeding period; feeding the first ruminant about one to about thirty grams of a supplemental feed material during the pre-weaning feeding period, the supplemental feed material comprising hemicellulose, and providing the first ruminant with a dry animal feed composition during a post-weaning feeding period, the method effective to cause the first ruminant to gain more weight during the post-weaning feeding period than a second ruminant gains during the post-weaning feeding period, where the second ruminant is also provided with the dry animal feed composition during the post-weaning feeding period, all feed provided to the second ruminant during the pre-weaning feeding period being free of the supplemental feed material.

39. The method of claim 38 wherein the second ruminant consumes about 1.25 pounds, or less, of the milk replacer per day, on a dry matter basis, during a first segment of the preweaning feeding period, the first ruminant consuming more of the milk replacer per day during the first segment of the pre-weaning feeding period than the second ruminant may consume per day during the first segment of the pre-weaning feeding period, on a dry matter basis, the milk replacer fed to the first ruminant having a greater concentration of protein than the milk replacer fed to the second ruminant, and the dry animal feed composition provided to the first ruminant having a greater concentration of protein than the dry animal feed composition provided to the second ruminant.

40. A method of feeding ruminants, the method comprising:
feeding a first ruminant an effective amount of milk replacer during a pre-weaning feeding period; and feeding the first ruminant about one to about thirty grams of a supplemental feed material during the pre-weaning feeding period, the supplemental feed material comprising hemicellulose, wherein: the method is effective to increase the amount of weight gained by the first ruminant during a post-weaning feeding period as compared to the amount of weight gained by a second ruminant during the post-weaning feeding period; and feed provided to the second ruminant is free of the supplemental feed material, the second ruminant consuming about the same amount of the milk replacer, on a dry weight basis, during the pre-weaning feeding period as the first ruminant consumes during the pre-weaning feeding period.

41. A method of feeding ruminants, the method comprising:
feeding a first ruminant an effective amount of milk replacer during a pre-weaning feeding period; feeding the first ruminant about one to about thirty grams of a supplemental feed material during the pre-weaning feeding period, the supplemental feed material comprising hemicellulose,
and providing the first ruminant with a dry animal feed composition during a post-weaning feeding period, the method effective to cause the first ruminant to gain more weight during a composite feeding period than a second ruminant gains during the composite feeding period, where the second ruminant is also provided with the dry animal feed composition during the post-weaning feeding period, all feed provided to the second ruminant during the pre-weaning feeding period is free of the supplemental feed material, and the composite feeding period comprises the pre-weaning feeding period and the post-weaning feeding period.

42. The method of claim 41 wherein the second ruminant consumes about 1.25 pounds, or less, of the milk replacer per day, on a dry matter basis, during a first segment of the pre-weaning feeding period, the first ruminant consuming more of the milk replacer per day during the first segment of the pre-weaning feeding period than the second ruminant may consume per day during the first segment of the pre-weaning feeding period, on a dry matter basis, the milk replacer fed to the first ruminant having a greater concentration of protein than the milk replacer fed to the second ruminant, and the dry animal feed composition provided to the first ruminant having a greater concentration of protein than the dry animal feed composition provided to the second ruminant.

43. A method of feeding ruminants, the method comprising:
feeding a first ruminant an effective amount of milk replacer during a pre-weaning feeding period; and feeding the first ruminant about one to about thirty grams of a supplemental feed material during the pre-weaning feeding period, the supplemental feed material comprising hemicellulose, wherein:
the method is effective to increase the amount of weight gained by the first ruminant during a composite feeding period as compared to the amount of weight gained by a second ruminant during the composite feeding period, the composite feeding period comprising the pre-weaning feeding period and a post-weaning feeding period; and
feed provided to the second ruminant is free of the supplemental feed material, the second ruminant consuming about the same amount of the milk replacer, on a dry weight basis, during the pre-weaning feeding period as the first ruminant consumes during the pre-weaning feeding period.

44. A method of feeding ruminants, the method comprising:
feeding a first ruminant a fluid animal feed composition during a pre-weaning feeding period, the fluid animal feed composition comprising a milk replacer; and feeding the first ruminant a supplemental feed material during the pre-weaning feeding period, the supplemental feed material comprising about 50 weight percent or more hemicellulose, based on the dry weight of the supplemental feed material, wherein:
a second ruminant consumes about 1.25 pounds or less of the milk replacer per day, on a dry matter basis, during the pre-weaning feeding period; the first ruminant consumes more of the milk replacer per day during the pre-weaning feeding period than the second ruminant may consume per day during the pre-weaning feeding period, on a dry matter basis;
all feed provided to the second ruminant during the pre-weaning feeding period is free of the supplemental feed material; and the method is effective to increase the feed efficiency of the first ruminant during the pre-weaning feeding period by 25 percent or more, as compared to the feed efficiency of the second ruminant during the pre-weaning feeding period.

45. The method of claim 44 wherein the first ruminant consumes about 2.5 pounds or more of the milk replacer per day, on a dry matter basis, during the pre-weaning feeding period.

46. A method of feeding ruminants, the method comprising:
feeding a first ruminant a fluid animal feed composition during a pre-weaning feeding period, the fluid animal feed composition comprising a milk replacer;
providing the first ruminant with dry animal feed composition during the pre-weaning feeding period; and
feeding the first ruminant a supplemental feed material during the pre-weaning feeding, the supplemental feed material comprising 50 weight percent or more hemicellulose, based on the dry weight of the supplemental feed material, wherein:
a second ruminant consumes about 1.25 pounds or less of the animal feed component per day, on a dry matter basis, during the pre-weaning feeding period;
the first ruminant consumes more of the milk replacer per day during the pre-weaning feeding period than the second ruminant may consume per day during the preweaning feeding period, on a dry matter basis;
dry animal feed composition is also provided to the second ruminant during the preweaning feeding period;
all feed provided to the second ruminant during the pre-weaning feeding period is free of the supplemental feed material;
the milk replacer fed to the first ruminant has a greater concentration of protein than the milk replacer fed to the second ruminant;
the dry animal feed composition provided to the first ruminant during the preweaning feeding period has a greater concentration of protein than the dry animal feed composition provided to the second ruminant during the preweaning feeding period; and
the method is effective to cause the first ruminant to gain about 64% or more additional weight during the pre-weaning feeding period, as compared to the weight gained by the second ruminant during the pre-weaning feeding period.

47. The method of claim 46 wherein the first ruminant consumes about 2.5 pounds or more of the milk replacer per day, on a dry matter basis, during the pre-weaning feeding period.

48. A method of feeding ruminants, the method comprising:
- feeding a first ruminant a fluid animal feed composition during a pre-weaning feeding period, the fluid animal feed composition comprising a milk replacer;
- feeding the first ruminant a supplemental feed material during the pre-weaning feeding period, the supplemental feed material comprising about 50 weight percent or more hemicellulose, based on the dry weight of the supplemental feed material; and
- providing the first ruminant with dry animal feed composition during a post-weaning feeding period, wherein: a second ruminant consumes about 1.25 pounds or less of the milk replacer per day, on a dry matter basis, during the pre-weaning feeding period;
- the first ruminant consumes more of the milk replacer per day during the preweaning feeding period than the second ruminant may consume per day during the pre-weaning feeding period, on a dry matter basis;
- dry animal feed composition is also provided to the second ruminant during the postweaning feeding period; all feed provided to the second ruminant is free of the supplemental feed material; the milk replacer fed to the first ruminant has a greater concentration of protein than the milk replacer fed to the second ruminant;
- the dry animal feed composition provided to the first ruminant during the postweaning feeding period has a greater concentration of protein than the dry animal feed composition provided to the second ruminant during the postweaning feeding period; the method is effective to cause the first ruminant to gain more weight during the post-weaning feeding period than the second ruminant gains during the postweaning feeding period.

49. The method of claim 47 wherein the first ruminant consumes about 2.5 pounds or more of the milk replacer per day, on a dry matter basis, during the pre-weaning feeding period.

50. A method of feeding ruminants, the method comprising:
- feeding a first ruminant a fluid animal feed composition during a pre-weaning feeding period, the fluid animal feed composition comprising a milk replacer;
- feeding the first ruminant a supplemental feed material during the pre-weaning feeding period, the supplemental feed material comprising about 50 weight percent hemicellulose or more, based on the dry weight of the supplemental feed material; and
- providing the first ruminant with dry animal feed composition during a post-weaning feeding period, wherein:
  - a second ruminant consumes about 1.25 pounds or less of the milk replacer per day, on a dry matter basis, during the pre-weaning feeding period;
  - the first ruminant consumes more of the milk replacer per day during the preweaning feeding period than the second ruminant may consume per day during the pre-weaning feeding period, on a dry matter basis;
  - dry animal feed composition is also provided to the second ruminant during the postweaning feeding period; all feed provided to the second ruminant is free of the supplemental feed material; the milk replacer fed to the first ruminant has a greater concentration of protein than the milk replacer fed to the second ruminant;
  - the dry animal feed composition provided to the first ruminant during the postweaning feeding period has a greater concentration of protein than the dry animal feed composition provided to the second ruminant during the postweaning feeding period; the method is effective to cause the first ruminant to gain more weight during a composite feeding period than the second ruminant gains during the composite feeding period, the composite feeding period comprising the preweaning feeding period and the post-weaning feeding period.

51. The method of claim 50 wherein the first ruminant consumes about 2.5 pounds or more of the milk replacer per day, on a dry matter basis, during the pre-weaning feeding period.

52. The method of claim 35 wherein the supplemental feed material is in powdered form.

53. The method of claim 35 wherein the supplemental feed material predominantly comprises hemicellulose.

54. The method of claim 35 wherein the supplemental feed material comprises a psyllium composition.

55. The method of claim 36 wherein the supplemental feed material is in powdered form.

56. The method of claim 36 wherein the supplemental feed material predominantly comprises hemicellulose.

57. The method of claim 36 wherein the supplemental feed material comprises a psyllium composition.

58. The method of claim 38 wherein the supplemental feed material is in powdered form.

59. The method of claim 38 wherein the supplemental feed material predominantly comprises hemicellulose.

60. The method of claim 38 wherein the supplemental feed material comprises a psyllium composition.

61. The method of claim 40 wherein the supplemental feed material is in powdered form.

62. The method of claim 40 wherein the supplemental feed material predominantly comprises hemicellulose.

63. The method of claim 40 wherein the supplemental feed material comprises a psyllium composition.

64. The method of claim 41 wherein the supplemental feed material is in powdered form.

65. The method of claim 41 wherein the supplemental feed material predominantly comprises hemicellulose.

66. The method of claim 41 wherein the supplemental feed material comprises a psyllium composition.

67. The method of claim 43 wherein the supplemental feed material is in powdered form.

68. The method of claim 43 wherein the supplemental feed material predominantly comprises hemicellulose.

69. The method of claim 43 wherein the supplemental feed material comprises a psyllium composition.

* * * * *